(12) United States Patent
Li et al.

(10) Patent No.: US 11,622,738 B2
(45) Date of Patent: *Apr. 11, 2023

(54) PET/MRI INSERT SYSTEM

(71) Applicant: SHANGHAI UNITED IMAGING HEALTHCARE CO., LTD, Shanghai (CN)

(72) Inventors: Hongdi Li, Houston, TX (US); Qun Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 330 days.

This patent is subject to a terminal disclaimer.

(21) Appl. No.: 17/012,374

(22) Filed: Sep. 4, 2020

(65) Prior Publication Data
US 2020/0397392 A1 Dec. 24, 2020

Related U.S. Application Data

(63) Continuation of application No. 15/029,582, filed as application No. PCT/CN2015/086131 on Aug. 5, 2015, now Pat. No. 10,806,416.

(51) Int. Cl.
*A61B 5/055* (2006.01)
*A61B 6/00* (2006.01)
(Continued)

(52) U.S. Cl.
CPC .......... *A61B 6/4417* (2013.01); *A61B 5/004* (2013.01); *A61B 5/0035* (2013.01); *A61B 5/055* (2013.01);
(Continued)

(58) Field of Classification Search
CPC ....... A61B 5/0035; A61B 5/004; A61B 5/055; A61B 6/037; A61B 6/0435; A61B 6/502;
(Continued)

(56) References Cited

U.S. PATENT DOCUMENTS 5,308,439 A 5/1994 Cronin et al.
8,013,607 B2 9/2011 Demeester et al.
(Continued)

FOREIGN PATENT DOCUMENTS

CN 103908280 A 7/2014

OTHER PUBLICATIONS

International Search Report in PCT/CN2015/086131 dated Apr. 28, 2016, 4 pages.
(Continued)

*Primary Examiner* — Boniface Ngathi N
(74) *Attorney, Agent, or Firm* — Metis IP LLC

(57) ABSTRACT

The present disclosure relates to an insert system for performing positron emission tomography (PET) imaging. The insert system can be reversibly installed to an existing system, such that PET functionality can be introduced into the existing system without the need to significantly modify the existing system. The present disclosure also relates to a multi-modality imaging system capable for conducting both PET imaging and magnetic resonance imaging (MRI). The PET and MRI imaging can be performed simultaneously or sequentially, while the performance of neither imaging modality is compromised for the operation of the other imaging modality.

20 Claims, 24 Drawing Sheets

(51) Int. Cl.
| | |
|---|---|
| G01R 33/48 | (2006.01) |
| G01V 5/00 | (2006.01) |
| A61B 5/00 | (2006.01) |
| G01R 33/3415 | (2006.01) |
| G01R 33/34 | (2006.01) |
| A61B 6/03 | (2006.01) |
| G01T 1/29 | (2006.01) |
| G01T 1/16 | (2006.01) |
| A61B 6/04 | (2006.01) |

(52) U.S. Cl.
CPC ............ *A61B 6/037* (2013.01); *A61B 6/0435* (2013.01); *A61B 6/502* (2013.01); *G01R 33/481* (2013.01); *G01T 1/1603* (2013.01); *G01T 1/2985* (2013.01); *G01V 5/0016* (2013.01); *A61B 6/4411* (2013.01); *G01R 33/3415* (2013.01); *G01R 33/34053* (2013.01); *G01R 33/34076* (2013.01)

(58) Field of Classification Search
CPC ................ A61B 6/4411; G01R 33/481; G01R 33/3415; G01T 1/20; G01T 1/249; G01T 1/2985
See application file for complete search history.

(56) References Cited

U.S. PATENT DOCUMENTS

| | | | |
|---|---|---|---|
| 8,073,525 | B2 | 12/2011 | Ladebeck et al. |
| 9,029,791 | B1 | 5/2015 | Kovalski et al. |
| 9,116,216 | B2 | 8/2015 | Nalcioglu et al. |
| 9,591,989 | B2 | 3/2017 | Tai |
| 10,806,416 | B2 * | 10/2020 | Li .................... A61B 6/0435 |
| 2004/0064046 | A1 | 4/2004 | Shehada |
| 2004/0249283 | A1 | 12/2004 | Kantorovich et al. |
| 2008/0077005 | A1 | 3/2008 | Piron et al. |
| 2008/0265887 | A1 | 10/2008 | Linz et al. |
| 2010/0074399 | A1 | 3/2010 | Majewski |
| 2012/0136237 | A1 | 5/2012 | Benlloch Baviera et al. |
| 2012/0271149 | A1 | 10/2012 | Tai |
| 2012/0330131 | A1 | 12/2012 | Nalcioglu et al. |
| 2013/0137964 | A1 | 5/2013 | Schellenberg |
| 2013/0241555 | A1 | 9/2013 | Obata et al. |
| 2014/0257093 | A1 | 9/2014 | MacDonald et al. |
| 2014/0275965 | A1 | 9/2014 | Majewski et al. |
| 2015/0002150 | A1 | 1/2015 | Weissler et al. |
| 2015/0008926 | A1 | 1/2015 | Yang et al. |

OTHER PUBLICATIONS

Written Opinion in PCT/CN2015/086131 dated Apr. 28, 2016, 6 pages.
Michael A. Ohliger et al., An Introduction to Coil Array Design for Parallel MRI, Nmr in Biomedicine, 19(3) 309-315, 2006.
Fujita H., New Horizons in MR Technology: RF Coil Designs and Trends, Magnetic Resonance in Medical Sciences, 6:29-42, 2007.
Anagha Deshmane et al., Parallel MR Imaging, Journal of Magnetic Resonance Imaging, 36:55-72, 2012.
David J Larkman et al., Parallel Magnetic Resonance Imaging, Physics in Medicine and Biology, 52:15-55, 2007.
Martin Blaimer et al., Smash, Sense, Pils, GRAPPA, How to Choose the Optimal Method. Top Magn Reson Imaging, 15:223-236, 2004.
Ze Wang et al., Improved Data Reconstruction Method for GRAPPA. Magnetic Resonance in Medicine, 54(3): 738-742, 2005.
Bo J Peng et al., Studies of the Interactions of an MRI System with the Shielding in a Combined PET/MRI Scanner, Physics in Medicine and Biology, 55(1): 265-280, 2010.
H. Malcolm Hudson et al., Accelerated Image Reconstruction Using Ordered Subsets of Projection Data, IEEE Transactions on Medical Imaging, 13(4): 601-609, 1994.
Ahmadreaz Rezaei et al., Simultaneous Reconstruction of Activity and Attenuation in Time-of-Flight PET, IEEE Transactions on Medical Imaging, 31(12): 2224-2233, 2012.
Arman Rahmim et al., Resolution Modeling in PET Imaging: Theory, Practice, Benefits and Pitfalls, Medical physics, 40(6): 064301-1-064301-14, 2013.
Bing Bai et al., Magnetic Resonance-Guided Positron Emission Tomography Image Reconstruction, Seminars in Nuclear Medicine, 43(1): 30-44, 2013.
Gudruo Wagenknecht et al., MRI for Attenuation Correction in PET: Methods and Challenges, Magn Reson Mater Phy, 26(1): 99-113, 2013.
C.C. Watson, New, Faster, Image-Based Scatter Correction for 3D PET, IEEE Transactions on Nuclear Science, 47(4): 1587-1594, 2000.
C.S. Levin et al., A Monte Carlo Correction for the Effect of Compton Scattering in 3-D PET Brain Imaging, IEEE Transactions on Nuclear Science, 42(4): 1181-1185, 1995.
Lampros Theodorakis et al., A Review of PET Normalization: Striving for Count Rate Uniformity, Nuclear Medicine Communications, 34(11): 1033-1045, 2013.
R.S. Miyaoka et al., Design of a Depth of Interaction (DOI) PET Detector Module, IEEE Transactions on Nuclear Science, 45(3): 1069-1073, 1998.
Mildko Ito et al., Positron Emission Tomography (PET) Detectors with Depth-of-Interaction (DOI) Capability, Biomedical Engineering Letters, 1(2): 70-81, 2011.
Cliff X. Wang et al., Performance Evaluation of Filtered Backprojection Reconstruction and Iterative Reconstruction Methods for PET Images, Computers in Biology and Medicine, 28(1): 13-25, 1998.
Partial Supplementary European Search Report in European Application No. 15896593.9 dated Jun. 6, 2018, 12 pages.
The Extended European Search Report in European Application No. 15896593.9 dated Sep. 21, 2018, 10 pages.
Ulrich Katscher et al., Parallel Magnetic Resonance Imaging, The Journal of the American Society for Experimental NeuroTherapeutics, 4(3):499-510, 2007.
Michel Defrise et al., Image Reconstruction Algorithms in PET, Positron Emission Tomography, 63-91, 2003.

* cited by examiner

PET/MRI INSERT SYSTEM

CROSS-REFERENCE TO RELATED APPLICATIONS

This application is a continuation application of U.S. patent application Ser. No. 15/029,582, filed on Apr. 14, 2016, which is U.S. national stage entry under 35 U.S.C. § 371 of International Application No. PCT/CN2015/086131, filed on Aug. 5, 2015, designating the United States of America, the entire contents of each of which are hereby incorporated by reference.

TECHNICAL FIELD

This application relates to non-invasive imaging technology, including positron emission tomography (PET) and magnetic resonance imaging (MRI). This application also relates to multi-modality imaging technology that integrates different structural and/or functional imaging mechanisms into a single system. Particularly, this application relates to the PET insert technology, which provides an easy way where PET functionality can be introduced into an existing system without the need to modify the system significantly.

BACKGROUND

Positron emission tomography (PET) is a specialized radiology procedure that generates and examines three-dimensional images of functional processes in a target organ or tissue of a body. Specifically, in PET studies, a biologically active molecule carrying a radioactive tracer is first introduced to a patient's body. The PET system then detects gamma rays emitted by the tracer and constructs a three-dimensional image of the tracer concentration within the body by analyzing the detected signal.

Because the biologically active molecules used in PET studies are natural substrates of metabolism at the target organ or tissue, PET can evaluate the physiology (functionality) and anatomy (structure) of the target organ or tissue, as well as its biochemical properties. Changes in these properties of the target organ or tissue may provide essential information for the identification of the onset of a disease process before any anatomical changes related to the disease become detectable by other diagnostic tests, such as computed tomography (CT) or magnetic resonance imaging (MRI).

In the field of breast cancer prevention and diagnosis, several PET imaging modalities have been developed to better screen for and stage breast cancer. Positron emission mammography (PEM) is a form of PET that produces a higher resolution image of a limited section of the body, namely the breast, than would be achievable by regular PET studies. Current PEM scanners typically contain a pair of compression paddles, to which PET detectors are mounted. Under the direction of a trained medical staff, a patient would place her breast(s) between a pair of compression paddles. Gentle compression is then applied such that all breast tissues are gently pulled and collected between the PET detectors for examination.

The unique high sensitivity of PET—in the picomolar range—allows detection of even minute amounts of radiolabeled markers in vivo, making PET the modality of choice for molecular imaging. In this respect, an important new perspective in the field of nuclear imaging was created by using PET in conjunction with other diagnostic tests to realize simultaneous acquisition of both structural and functional information of the body and provide more definitive information about malignant (cancerous) tumors and other lesions. For example, since the introduction of combined PET/CT (computed tomography) systems about 10 years ago, medical practitioners in the fields of oncology, neurology, cardiology and radiology have been taken advantages of the dual-modality system to construct and analyze three-dimensional functional PET images in comparison with structural x-ray CT images that are obtained almost simultaneously with a same PET/CT scanner in a single session.

To this end, there are many clinical indications where magnetic resonance imaging (MRI) is preferred over CT. For example, MRI offers, compared to CT, better soft tissue contrast and does not use ionizing radiation, thus significantly reducing the overall required radiation doses and associated risk or harm to a patient. Furthermore, in addition to structural imaging, MRI can also be used to visualize functional activity of the body. For example, functional MRI or fMRI, measures changes in blood flow to different parts of the brain. In this type of studies, signals reflecting the blood-oxygen levels in the brain can be reliably used as a proxy for brain activity, because neurons use more oxygen when they are active.

Thus, the current need in the field of non-invasive diagnostic imaging to accurately and transparently combine high resolution, three-dimensional functional PET information with equally high quality morphological and/or functional MRI information within a single device establishes a clear new direction for research and development of next generation multi-modality imaging technology.

A PET/MR hybrid system capable of simultaneous dual-modality imaging would provide many advantages which go far beyond simply combining separately acquired PET and MRI data. These advantages include not only great convenience, flexibility, and improved speed for multi-modality acquisition of more data, but also much simplified logistics of patient management and significantly reduced patient costs. More importantly, simultaneous multi-modality data acquisition and processing ensure far greater accuracy in registration of PET and MRI data, hence providing medical practitioners more detailed and reliable diagnostic information.

However, despite great endeavor in the field, several technical difficulties continue to exist and hinder the realization of full PET/MR integration and real simultaneous data acquisition. Particularly, PET and MRI are two advanced imaging technologies, which require collecting and processing electronic signals that are delicate and prone to interference. Thus, combining the two modalities without degrading the original optimum performance of either is challenging. Furthermore, another major challenge exists with the integration of hardware components into a single device, overcoming physical constrains on available space.

To solve the problem of signal distortion and associated degradation of performance of the imaging modalities, different methods have been proposed and tried in the field. Many of the proposed methods aim at reducing mutual signal interference by enlarging physical distances between various hardware components of the PET/MR hybrid system. However, this approach could significantly reduce detection sensitivity of one or both imaging modalities, and would further aggravate the problem of space restrain as well. Other approaches aim only at hardware integration without taking simultaneous data acquisition into consideration. That is, even though diagnostic imaging with both MRI and PET may be accomplished using a single device in one session, data acquisition by the dual imaging modalities are sequential rather than simultaneous. For example, an in-line solution would mechanically combine a standard MRI with a standard PET scanner in a tandem fashion. As such, a patient's body would first go through the MRI scanner and then the PET scanner. Alternatively, PET components can be integrated into the MRI gantry, but the PET data is acquired only when the magnetic fields of MRI is completely turn off. Either imaging protocols would not allow real simultaneous PET/MR hybrid imaging. In addition, the total imaging time for the sequential PET and MRI scans is prolonged.

Thus, there exists a need in the field to provide an improved multi-modality diagnostic imaging technology that overcomes the various aforementioned technical challenges.

SUMMARY OF THE INVENTION

One objective of the present disclosure is to provide a new multi-modality imaging system that allows truly simultaneous PET and MR imaging while achieving the same or even better performance and specifications similar to their stand-alone imaging counterparts. Particularly, simultaneous data acquisition of the present system enables essentially perfect temporal correlation of dynamically acquired structural and functional data sets from both modalities.

Another objective of the present disclosure is to provide a new multi-modality imaging system that offers improved signal detection sensitivity for both PET and MRI imaging, as well as various hardware and software features to realize near-complete elimination and/or correction of mutual interference between PET and MRI imaging modalities.

Another objective of the present disclosure is to provide a multi-modality imaging system that is particularly suitable for examining the mammary gland or breast(s) of a human subject.

Another objective of the present disclosure is to provide a PET insert system that can be conveniently installed to an existing system without the need of significantly modifying the system's structure, operation and functionality, thus reducing cost to the user, including, researchers, hospitals and patients.

Yet, another objective of the present disclosure is to provide a PET insert system that offers end users great flexibility in arranging the PET detectors according to particular needs, such as to acquire optimum imaging signal and data or to perform biopsy while the image subject remains in the same position as during the imaging study.

Accordingly, in one aspect of the present disclosure, a PET insert system is provided. The insert system comprises a PET detector. In some embodiments, the PET detector comprises a plurality of detection blocks, each detection block having a scintillator face, and the scintillator face of each detection block opposes the scintillator face of at least one other detection block. In some embodiments, the plurality of detection blocks surround a sample area that is adapted for holding a target body.

In some embodiments, the plurality of detection blocks of the PET insert system form one or more opposing pairs, and each opposing pair of detection blocks flank the sample area.

In some embodiments, the PET detector comprises four detection blocks. The four detection blocks surround the sample area in a cubic column configuration with each detection block perpendicular to two other detection blocks.

In some embodiments, the PET detector comprises eight detection blocks. The eight detection blocks form a first set of four detection blocks and a second set of four detection blocks, and the sample area comprises a first sub-area and a second sub-area. The first set of four detection blocks surround the first sub-area in cubic column configuration, and the second set of four detection blocks surround the second sub-area in cubic column configuration.

In some embodiments, the PET detector comprises eight detection blocks, and the eight detection blocks surround the sample area in a barrel-shaped configuration with each detection block facing a separate octant of a 360-degree field.

In some embodiments, at least one detection block is capable of being removed from the PET detector, and the sample area is accessible upon removal of the detection block.

In some embodiments, the PET insert system further comprises a control system and/or a power supply.

In some embodiments, the PET insert system is adapted for reversibly coupling to a main system.

In some embodiments, when the PET insert system is reversibly coupled to the main system, the PET detector is reversibly attached to a patient support of the main system.

In some embodiments, the main system is capable of MR imaging of the target body. In some embodiments, the main system is a multi-modality imaging system.

In some embodiments, the target body is breasts of a human subject.

In second aspect of the present disclosure, a multi-modality imaging system is provided. Particularly, in some embodiments, the multi-modality imaging system comprises at least a PET imaging modality and a MR imaging modality, wherein the PET imaging modality and the MR imaging modality are capable of sequential or simultaneous operation.

In some embodiments, the MR imaging modality comprises a RF transmitter and a RF receiver. The RF transmitter is adapted for delivering excitation electromagnetic radiation to the target body, and the RF receiver is adapted for detecting nuclear magnetic resonance signal from the target body.

In some embodiments, the RF transmitter comprises a coil system. In some embodiments, the RF receiver also comprises a coil system. Further in some embodiments, the coil system of the RF transmitter and the coil system of the RF receiver are the same.

In some embodiments, one or both of the coil system of the RF transmitter and the coil system of the RF receiver are multi-channel coils.

In some embodiments, one or both of the coil system of the RF transmitter and the coil system of the RF receiver are phased-array coils.

In some embodiments, one or both of the coil system of the RF transmitter and the coil system of the RF receiver are local coils.

In some embodiments, one or both of the coil system of the RF transmitter and the coil system of the RF receiver are volume coils.

In some embodiments, the coil system of the RF transmitter is a volume coil and the coil system of the RF receiver is a local coil.

In some embodiments, the PET imaging modality of the multi-modality imaging system comprises a PET detector. The PET detector surrounds a sample area adapted for holding the target body.

In some embodiments, one or both of the coil system of the RF transmitter and the coil system of the RF receiver are located within the sample area.

In some embodiments, the target body is breasts of a human subject, and one or both of the coil system of the RF transmitter and the coil system of the RF receiver are adapted to surround the breasts in the sample area.

In some embodiments, the target body is breasts of a human subject, and one or both of the coil system of the RF transmitter and the coil system of the RF receiver are adapted to surround the chest circumference of the human subject in the sample area.

In some embodiments, the PET imaging modality of the multi-modality imaging system is a PET insert system.

BRIEF DESCRIPTION OF THE DRAWINGS

The accompanying drawings, which are incorporated in and constitute a part of this specification, illustrate several aspects described below.

DETAILED DESCRIPTION

Figure 1:
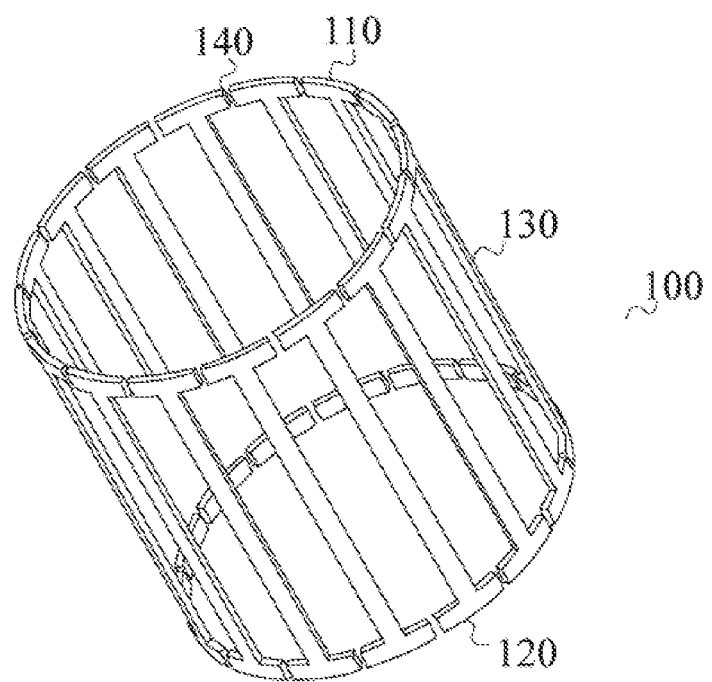
FIG. 1 is a perspective view of a multi-channel birdcage coil that may be used in connection with the present system according to one embodiment of the present disclosure.

After reading this description, it will become apparent to one skilled in the art how to implement the disclosure in various alternative embodiments and alternative applications. However, not all embodiments of the present disclosure are specifically described herein. It will be understood that the embodiments are presented by way of example only, and not limitation. As such, this detailed description of various alternative embodiments should not be construed to limit the scope or breadth of the present invention as set forth below.

Before the present invention is disclosed and described, it is to be understood that the aspects described below are not limited to specific systems, methods of making such systems or uses thereof as such may of course vary. It is also to be understood that the terminology used herein is for the purpose of describing particular aspects only and is not intended to be limiting.

Unless defined otherwise, all technical and scientific terms used herein have the same meaning as commonly understood by one of ordinary skill in the art to which this disclosure belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a," "an" and "the" are intended to include the plural forms as well, unless the context clearly indicates otherwise.

Unless otherwise expressly specified, all numerical designations, e.g., pH, temperature, time, concentration, amounts, and weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the electronic, mechanical or chemical components described herein are merely exemplary and that equivalents of such are known in the art.

Optional" or "optionally" means that the subsequently described event or circumstance can or cannot occur, and that the description includes instances where the events or circumstance occurs and instances where it does not.

Provided herein are components and combinations of a multi-modality imaging system for non-invasive imaging use in the biomedical field, such as for disease diagnostic or research purposes. The multi-modality system comprises imaging modalities for conducting various different medical scans or studies, including but not limited to ultrasound scan, X-ray scan, bone densitometry, fluoroscopy, computed tomography (CT), magnetic resonance imaging (MRI) and positron emission tomography (PET).

The term "imaging modality" or "modality" as used herein broadly refers to an imaging method or technology that gathers, generates, processes and/or analyzes imaging information of a target body through a particular mechanism. Accordingly, a multi-modality imaging system of the present disclosure can include more than one imaging modality, such as two, three, or more different modalities. In a multi-modality system, the mechanisms through which different imaging modalities operate or function can be the same or different. Accordingly, the imaging information can also be the same or different. For example, in some embodiments, the imaging information can be internal and/or external information, and can be functional and/or structural information of the target body. Particularly, in some embodiments, the imaging information of different modalities complement one another, thereby providing a set of imaging data describing a target body from different analytical angles. For example, in some embodiments, the multi-modality imaging achieves merging of morphological and functional images.

For example, in some embodiments, the multi-modality system includes a computed tomography (CT) imaging modality, which is a medical imaging method that combines multiple X-ray projections taken from different angles to produce detailed cross-sectional images of internal areas of the target body. Thus, CT imaging information offers medical practitioners precise, three-dimensional views of certain internal parts of the target body, such as soft tissues, bones, blood vessels, important organs of a human body, without performing invasive procedures on the target body. In some embodiments, the multi-modality system includes an ultrasound imaging modality, which is a medical imaging technology that uses high frequency sound waves to create images of the internal of the target body. Particularly, in some embodiments, the ultrasound imaging modality sends sound waves into the body and is able to convert the returning sound echoes into an image. In some embodiments, an ultrasound imaging modality can be used to diagnose abnormalities in the heart and blood vessels and assess conditions of pregnancy, health of organs in the pelvis and abdomen, or symptoms of pain, swelling and infection of a human subject. In some embodiments, the multi-modality system includes an X-ray imaging modality, which is an imaging technology that uses ionizing radiation to produce images of a target body's internal structure by sending X-ray beams through the target body, which are absorbed in different amounts depending on the density of the material.

MR Imaging Modality

In some embodiments of the present disclosure, the multi-modality imaging system comprises imaging modules and components for conducting MR imaging and analysis. MRI is a non-invasive imaging technique that uses a powerful magnet to align the nuclei of atoms inside a target body, and a variable magnetic field that causes the atoms to resonate, a phenomenon called nuclear magnetic resonance. The nuclei produce their own rotating magnetic fields that a scanner detects and uses to create an image of internal of the target body. The term "target body" as used herein broadly relates to any organic or inorganic mass, natural or man-made, that has a chemical, biochemical, biological, physiological, biophysical and/or physical activity or function. Exemplary embodiments of a target body pertaining to the present disclosure include cells, tissues, organs or whole bodies of human or animal. Other exemplary embodiments include but not limited to man-made composition of organic and/or inorganic matters that are with or without life.

Specifically, a MRI scanner typically includes three main parts, namely a system that generates a static homogenous magnetic field, sometimes referred to as the main magnetic field; a system that generates and receives radiofrequency (RF) radiation; and a system that generates a magnetic gradient field, i.e., a magnetic field with varying strength along one direction.

Particularly, when the MRI scanner applies the strong magnetic field to a target body, the applied field has a tendency to align magnetic moments (spins) of nuclei in the target body along the magnetic field. Strength of the main magnetic field may vary within the range of 0.5 to 4 tesla. The main magnetic field may be generated by various types of magnets, including, but not limited to, a superconducting magnetic, a resistive magnet, and a non-electrical permanent magnet. In some embodiments, the earth magnetic field can be used as the main magnetic field.

Many atomic nuclei of interest in MRI studies have their characteristic resonant frequencies in the RF range of the electromagnetic spectrum. Thus, after the main magnetic field has been applied to align the nuclei in the target body, the MRI scanner produces a RF current that creates an oscillating electromagnetic field. When the frequency of the oscillating electromagnetic field matches the characteristic resonant frequency of the aligned nuclei, the aligned nuclei absorb the energy of the oscillation electromagnetic field and flip their spins. Subsequently, the RF electromagnetic field is turned off, and the nuclei gradually return to their original spin in a process known as precession or relaxation. The return process produces the nuclear magnetic resonance (NMR) signal, which leaves the target body as RF electromagnetic radiation and can be measured by the MRI scanner and made into an image.

Not intended to be limiting, in some embodiments, the nuclei that are responsible for producing the NMR signals are hydrogen nuclei (protons) in water. For example, when imaging human body, water accounts for about 60-70% of the body weight. Protons in different body tissues return to their normal spins at different rates, so the MRI scanner can distinguish among tissues. The nuclei that can be utilized for MR imaging and analysis described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims.

In some embodiments of the present disclosure, the imaging system includes one or more RF coils or coil assemblies for transmitting the machine-generated RF radiation to and/or receiving the NMR signal from the target body during MRI.

The term "coil" as used herein generally refers to an electrical conductor, such as a wire, in the shape of a circle, coil, spiral or helix. In some embodiments of the present disclosure, the coils have applications where electric currents interact with magnetic fields. For example, either an electric current is passed through the conductor of the coil to generate a magnetic field, or conversely, an external magnetic field generates an electrical current in the conductor. The term "Radio-frequency coil" or "RF coil" as used herein thus refers to coils that operate with alternating currents in the radio frequency range.

In some embodiments of the present disclosure, the transmitting and receiving functions are performed by one or more RF coils or coil assemblies of the system. Particularly, when used as a transmitting coil, the RF coil generates an oscillating magnetic field in response to an alternating current flowing through. The current is generated by the MRI scanner's transmit circuitry. The current and hence the oscillating magnetic field is usually turned on for only brief periods of time, in the range of milliseconds, and thus is sometimes referred to as the "RF pulses." By adjusting the magnitude or duration of the RF pulses, the spin of the nuclei of interest can be rotated by variable flip angles, such as 90 or 180 degrees. On the other hand, when used as a receiving coil, the RF coil is responsible for detecting the NMR signal. Particularly, the electromagnetic radiation emitted from the target body during relaxation of the spin system induces an oscillating electric current in the RF coil, and thus is captured. In some embodiments, this current is subsequently amplified, digitized and/or analyzed.

Depending on the size and function, RF coils for MRI can be generally classified as volume coils and local coils. The term "volume coil" as used herein generally refers to coils that are used to provide a homogenous RF excitation field across a relative large volume, such as to cover the entire target body. For example, many commercially available MRI scanners include a volume coil that is big enough for whole body imaging of a human subject, thus sometimes is referred to as the "body coil." Smaller volume coils can also be used for imaging a portion of the human body, such as the head, a limb, an extremity or the trunk. In some embodiments, the MR imaging modality of the present system may include one or more volume coils of different sizes and functions. In some embodiments, a volume coil is built in with the system, such as incorporated into the bore or tunnel of a MRI scanner where a patient passes through during a scan. In some embodiments, a volume coil of the present system is provided as an installable component, for example, as an accessory, which can be selectively installed to or uninstalled from the system according to the specific needs.

Coils of various different geometry can be used as a volume coil for MRI, which include but are not limited to birdcage coils, transverse electromagnetic (TEM) coils, surface coils and saddle coils. In some embodiments, a birdcage coil contains two circular conductive loops referred to as end rings connected by an even number of conductive straight elements called rungs or legs. The number of rungs depends on the size of the coil and may range from about 8 to 32. In some embodiments, a birdcage coil also contains capacitors between conducting elements variably arranged based on the frequency characteristics desired. For example, in some embodiments, a birdcage coil has pairs of capacitors located along the end rings to form a high-pass configuration, so as to approximate a continuous conducting surface. An exemplary birdcage coil that can be used in connection with the present disclosure is described in Example 1.1. The structure and geometry described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims. For example, a TEM coil may have an architecture similar to that of a birdcage coil, but instead of having conductive end rings. The TEM coil has a slotted cavity for the return path of the rung elements, rendering the TEM coil as an array of independent transmission line element resonators.

In some embodiments, a saddle coil has a cylindrical body, including two symmetrical halves with one or more turns of wire or foil on each half. For example, the cylindrical body of a saddle coil can contain four linear segments and four circular arcs on the cylindrical body. A saddle coil can be made by one wire forming one turn in each half or can be made by two wires separately forming one turn in each half. By two linear segments running current in one direction and other two linear segments running current in the opposite direction, the saddle coil generates a highly homogenous magnetic field perpendicular to the linear segments.

As can be appreciated from the present disclosure, volume coils of different geometry can generate highly homogenous RF excitation field across a relatively large portion of or even the entire target body. However, the use of volume coils may be less ideal when the MRI region of interest (ROI) is relatively small as compared to the size of the target body. This is because volume coils have a relatively large field of view (FOV), which receives noises from the whole target body, rather than just the region of interest. Thus, volume coils tend to have a low signal to noise ratio (SNR) for imaging of small ROI.

Accordingly, in some embodiments, small local coils are used for imaging small ROIs. The term "local coil" as used herein generally refers to coils that are to be placed in close proximity to the region of interest during MR imaging. In some embodiments, local coils are designed to achieve improved RF detection sensitivity over a small region of interest. Particularly, in some embodiments, local coils can be arranged with respect to the target body in a manner that it closely contacts or surrounds the region of interest.

As can be appreciated by one of ordinary skill in the art, coils of much different geometry may be used as a local coil. Exemplary embodiments of local coils that can be used in connection with the present system include, but are not limited to, a surface coil, a birdcage coil, a solenoid coil, a saddle coil, a flexible coil or various combinations thereof. The geometry of local coils described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims. For example, in some embodiments, a surface coil is essentially a single turn loop of conducting material, such as a cooper wire. In alternative embodiments, a surface coil can have multi-turn loops. The loop may form various shapes and/or be bent slightly to conform to the profile of the part of the target body to be imaged. The size of the loops can be optimized for the specific region of interest.

In some embodiments, when used as a receiving coil, a surface coil can be placed on, over or surrounding the region of interest for increased electromagnetic sensitivity, because the spatial extent of the excitation or reception is limited. That is, only regions of a target body that are close to the surface coil contribute to the NMR signal received by the coil, thus the signal to noise ratio for these regions is improved as compared to the use of receiving coils that surround the whole target body, such as a volume coil.

In some embodiments, the local coil closely surrounds the region of interest of a target body. For example, for imaging a human subject, a local coil can surround the tissue of interest, such as one or both breasts of a female patient for examination of the mammary gland. In some embodiment, the local coils specifically designed for imaging the mammary gland are referred to as the breast coils. In some embodiments, during an imaging session, a female subject lies in the prone position on a chest support structure. A breast coil is placed underneath the chest support, such that the subject can insert one of her breasts through the chest support to be closely surrounded by the breast coil. In some embodiments, a pair of breast coils are placed under the chest support, such that both sides of the subject's breasts can be examined at the same time. In some embodiments, a single breast coil is designed to surround both breasts at the same time. In some embodiments, instead of surrounding only the breast tissue, a breast coil is designed to surround the subject's entire chest circumference, with the coil turn(s) placed over the subject's breast tissues. The geometry and arrangements of breast coils described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims. Depending on the breast coil used, a subject can take various different gestures during an examination session, such as standing, sitting, lying on the back, side or in a prone position.

As can be appreciated from the present disclosure, small coils have better signal-to-noise ratio and thus high detection sensitivity for NMR signals, but at the same time limited structural coverage. On the other hand, large coils provide large fields of view with compromised signal sensitivity. Accordingly, in some embodiments of the present disclosure, small coils are combined into a large assembly, such that it is possible to obtain both advantages of a high signal-to-noise ration and large fields of view.

The term "coil assembly" as used herein refers to a set of coils arranged in a particular architecture with respect to one another, such that the set of coil can perform a concerted function for transmitting and/or receiving RF radiations in MRI. Coil assemblies that can be used in connection with the present system can be either a single or a multi-channel coil system.

The term "multi-channel coil" as used herein generally refers to any architecture of coil or coil assemblies where the coil or coil assembly contains multiple independent signal transmission circuitries, which circuitries can be independently controlled, thereby enabling a much more precise manipulation over the coil's or coil assembly's operation. Accordingly, a multi-channel coil or coil assembly enable much precise control over the electromagnetic signal in terms of its magnitude, phase, space, time and frequency comparing to conventional single-channel coils. Thus, when used as RF transmitting coils, a multi-channel coil or coil assembly enables the generation of a RF field to canvas a large target body that could otherwise not be uniformly excited. When used as RF receiving coils, a multi-channel coil or coil assembly collects both intensity and phase information of the electromagnetic signal with uniform detection sensitivity across the entire field of view. Other advantages of a multi-channel coil include improved data acquisition speed and sensitivity and the ability of conducting parallel imaging. Specifically, parallel magnetic resonance imaging is described in Katscher U1, Parallel magnetic resonance imaging. Neurotherapeutics. 2007 July; 4(3):499-510 which article is incorporated herein by reference in its entirety.

Particularly, in some embodiments, the coil assembly is an array coil system, which is a collection of small local coils whose signals may be either combined into a single channel or kept separate in multiple channels. Array coil systems of different architectures and mechanisms of operation can be used in connection with the present system.

For example, in some embodiments, the coil assembly is a phased-array system. The term "phased array" derives from but is by no means limited by the antenna theory where large groups of small antennas are coupled together and used to enhance overall signal or transmission properties. A phased-array system can include multiple coils with separate transmission circuitries, such that the phase information of signals transmitted or received by the individual coils are separately controlled and/or monitored.

A phased-array coil system can be used for either or both of RF transmitting and receiving. Accordingly, in some embodiments, the use of a phased-array system for RF transmitting enables the generation of a homogenous excitation field across a much larger field of view than that of a single coil. In some embodiments, the use of a phased-array coil system for RF receiving allows for a significantly improved signal-to-noise ratio. Particularly, in some embodiments, a phased-array system containing N independent coils, each with their own preamplifier and transmission channel can increase the signal-to-noise ratio by a factor of square root of N. For example, a four-coil phased array system could achieve 2 times higher signal-to-noise ratio than that of a single coil. In some embodiments, the use of a phased-array coil system allows the decreasing of the number of signal averages, which shortens the scan time by high signal-to-noise ratio and resolution.

In some embodiments, the phased-array system includes 2 coils. In other embodiments, the phased array system can include more than 2 coil. For example, in some embodiments, the phased array system can include 4-32 coils. In other embodiments, the phased array system can include 1-128 or even more coils.

In some embodiments, a phased-array system employs a linear array of single-turn surface coils, where adjacent coils overlap to minimize coupling between themselves. In some embodiments, a phased-array system further includes preamplifiers for isolating the relatively weak coupling between non-adjacent coils. Particularly, in these embodiments, the individual single-turn surface coils can have loops of various different shapes, including but not limited to polygon, circle, oval and irregular shapes.

In some embodiments, a phased-array system employs a stacked array of single-turn coils. For example, in some embodiments, the array of individual coils can have the same loop shape, and each coil is placed next to at least one other coil along a common axis.

In some embodiments, a phased-array system employs the birdcage configuration, such as described above in relation to the volume coil embodiments, and illustrated in Example 1.1. The structure, geometry and arrangements of phased array system described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims such as those described in Ohliger et al., *An introduction to coil array design for parallel MRI*. NMR in Biomedicine, 2006, 19(3): 300-315, Fujita H. *New horizons in MR technology: RF coil designs and trends*. Magn Reson Med Sci 2007; 6:29-42, which articles are incorporated herein by reference in their entirety.

In some embodiments, the coil or coil assembly used in connection with the present system is suitable for parallel imaging. Digital processing algorithms for parallel imaging that speed up image acquisition and reconstruction during the MRI scan are known in the art. Fast parallel imaging techniques, for example sensitivity encoding (SENSE), "Partially Parallel Imaging with Localized Sensitivity" (PILS), Simultaneous Acquisition of Spatial Harmonics "SMASH" or Array Spatial Sensitivity Encoding Technique "ASSET" can be used in connection with multi-channel phased-array coil systems to further improve spatial and temporal resolution. The processing algorithms that can be used in connection with the present system described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims such as those described in Deshmane A et al., *Parallel MR imaging*. J Magn Reson Imaging 2012; 36:55-72, Larkman D J, Nunes R G. *Parallel magnetic resonance imaging*. Phys Med Biol 2007; 52:R15-R55, Blaimer M et al., *SMASH, SENSE, PILS, GRAPPA. How to choose the optimal method*. Top Magn Reson Imaging 2004; 15:223-236, and Wang et al. *A. Improved data reconstruction method for GRAPPA*. Magnetic resonance in medicine, 2005, 54(3): 738-742. which articles are incorporated herein by reference in their entirety.

In some embodiments, the RF transmitting and receiving functions are performed by the same RF coil or coil assembly. Yet, in alternative embodiments, the RF transmitting and receiving functions are performed by separate RF coils or coil assemblies. For example, in some embodiments, a volume coil or coil assembly acts as both the RF transmitter which generates the RF pulses and sends the excitation energy to the target body and the RF receiver which receives NMR signal from the target body. In some embodiments, a local coil or coil assembly acts as both the RF transmitter and the RF receiver. In other embodiments, a volume coil or coil assembly acts as the RF transmitter while a local coil or coil assembly acts as the RF receiver. In other embodiments, a local coil or coil assembly acts as the RF transmitter, while a volume coil or coil assembly acts as the RF receiver. In some embodiments, multiple volume coils or coil assemblies act as the RF transmitter and the RF receiver, respectively. Yet, in other embodiments, multiple local coils or coil assemblies act as the RF transmitter and the RF receiver, respectively.

A RF transmitting coil or coil assembly and a RF receiving coil or coil assembly used in the present system can have the same or different configurations. Single-channel coil or coil assemblies can be used for either RF transmitting or RF receiving or both. Similarly, multi-channel coil or coil assemblies can be used for either RF transmitting or RF receiving or both.

For example, in some embodiment a local multi-channel birdcage coil can be used for both RF transmitting and receiving. In some embodiment, a local multi-channel birdcage coil can be used for RF transmitting and a local multi-channel phased-array coil assembly can be used for RF receiving. Example 1.2 illustrates an exemplary embodiment where a multi-channel birdcage coil and a multi-channel phased-array coil assembly having a pseudo-chain-link configuration are used for RF transmitting and RF receiving, respectively. Example 1.3 illustrates an exemplary embodiment where a multi-channel coil assembly having the stacked loop configuration is used for both RF transmitting and receiving. The particular embodiments as in Examples 1.2 and 1.3 may be used as local breast coils for examining mammary gland of a human subject.

Finally, a MRI scanner generates a magnetic gradient field that is used to provide localization information for three-dimensional image construction. In some embodiments, the system includes a gradient coil that offers a magnetic field linear variation along one direction. The variable gradients produce the spatial characteristics of an MR image. In some embodiments, more than one coils can be used to generate a gradient in one direction. In some embodiments, magnetic gradient can be generated along more than one directions. For example, in some embodiments, three sets of gradient coils can be used to generate gradients in three orthogonal directions.

PET Imaging Modality

In some embodiments of the present disclosure, the multi-modality imaging system further comprises modules and components for performing positron emission tomography (PET) imaging and analysis. The term "positron emission tomography or PET" as used herein refers to a non-invasive radiology procedure applicable to a target body that generates image information reflecting or corresponding to functional processes taking place in the internal body. The term "target body" as used herein broadly relates to any organic or inorganic mass, natural or man-made, that has a chemical, biochemical, biological, physiological, biophysical and/or physical activity or function. Exemplary embodiments of a target body pertaining to the present disclosure include cells, tissues, organs or whole bodies of human or animal. Other exemplary embodiments include but not limited to man-made composition of organic and/or inorganic matters that are with or without life.

PET Tracer

During a PET scan or study, a PET tracer molecule is first introduced into the target body before an imaging session begins. The term "PET tracer" or "tracer" as used herein refers to a substance that may undergo certain changes under the influence of an activity or functionality within the target body, which activity and functionality are to be visualized and studied by the PET. Such changes can be chemical and/or physical, during which the PET tracer emits positrons, namely the antiparticles of electrons. A positron has the same mass and the opposite electric charge as an electron, and it undergoes annihilations with an electron (that naturally exists in abundance within the target body) as the two particles collide. Typically, the electron-positron annihilations results in two 511 keV gamma photons, which upon their own generation, begin to travel in opposite directions with respect to one another. The PET imaging modules of the present system obtains the trajectory and dose information of the gamma photons to determine the location and concentration of the PET tracer molecules within the target body.

Many basic elements that make up organic matters have positron-emitting isotopes, including but not limited to carbon ($^{11}$C), nitrogen ($^{13}$N), oxygen ($^{15}$O) and fluorine ($^{18}$F). Accordingly, in some embodiments, the PET tracer molecules of the present disclosure are organic compounds containing one or more of those positron-emitting isotopes. These type of PET tracer molecules are either similar to naturally occurring substances or otherwise capable of interacting with the functionality or activity of interest within the target body. Hence, distributional information of the PET tracer can be reliably used as an indicator of the target body functionality.

For example, in some embodiments of the present disclosure, the PET tracer molecule is $^{18}$F-fluoro-deoxy-glucose ($^{18}$F-FDG), a radioactive analogue of glucose. $^{18}$F-FDG follows a similar metabolic pathway to glucose in vivo, but remains trapped within tissues. Thus, in vivo distribution of $^{18}$F-FDG mapped by the present PET imaging will indicate glucose metabolic activity, which can be of particular interest in oncology as proliferating cancer cell have higher than average rate of glucose metabolism. In other embodiments, the PET tracer molecule is $^{13}$N—NH$_3$ for functional imaging of myocardial perfusion. Particularly, in these embodiments, in vivo distribution of $^{13}$N—NH$_3$ can be used to distinguish between viable and non-viable tissue in poorly perfused areas of the heart, which information can be of particular interest in cardiology to identify candidates for coronary by-pass surgery.

Further provided below is a non-exhaustive list of exemplary embodiments of organic PET tracers that can be used in connection with the present system. Particularly, In some embodiments, the PET tracer molecule is $^{11}$C-methionine, where it acts as a marker for protein synthesis in oncology. In some embodiments, the PET tracer molecule is $^{11}$C-flumazenil, where it acts as a marker for benzodiazepine receptor activity in epilepsy. In some embodiments, the PET tracer molecule is $^{11}$C-raclopride, where it acts as a marker for D2 receptor agonist activity for diagnosis of movement disorders. In some embodiments, the PET tracer molecule is $^{15}$O-carbon dioxide or $^{15}$O-water, where it acts as a marker for blood perfusion in brains. In some embodiments, the PET tracer can be fluoride ion, where it acts as a marker for bone metabolism in oncology; in some embodiments, the PET tracer molecule is 18F fluoro-mizonidazole, where it acts as a marker for hypoxia in assessing patient response to radiotherapy in oncology. Yet, in other embodiments, multiple different PET tracers can be used in combination to produce complementing sets of functional data.

During a PET scan or study, a PET tracer molecule is first introduced into the target body before an imaging session begins. The administration of a PET tracer can be local or systematic. As used herein, the term "local administration" refers to the manner of administration through which the post-administration distribution of the PET tracer is limited to a portion or a sub-system within the target body. For example, in those embodiments where the target body is a human patient, the PET tracer can be administered in a way that post-administration distribution of the tracer only covers a certain portion of the human body, such as an internal organ, a gland or the immune system or subsystem, and for example, the liver, the mammary gland, or the lymph system of the patient.

Alternatively, the term "systematic administration" as used herein refers to the manner of administration through which the post-administration distribution of the PET tracer covers the entire target body. For example, in those embodiments where the target body is a human patient, the administration is performed in a manner that the administered tracer would travel from the site of administration to the entire body of the patient. Many administration methods can be used for the delivery of the PET tracer to the target body, including but not limited to those used in medical or clinical practices. A non-exhaustive list of exemplary embodiments of administration methods that can be used in connection with the present system includes topical administration, oral administration, intravenous administration, administration through inhalation, and targeted administration. For example, in some embodiments of the present disclosure, the tracer is administered to the target body via intravenous injection. The term "intravenous injection or i.v. injection" as used herein refers to a method for infusing fluid substances directly into a vein. In some embodiments, the process involves the use of a drip chamber to prevent air from entering the blood stream, therefore sometimes is referred to as a drip. In some embodiments, intravenous administration is used for local administration of the PET tracer, while in other embodiments, intravenous administration is used for systematic administration of the PET tracer. Advantages of intravenous injection include good bioavailability preservation, rapid action onset, and use for tracers that are poorly absorbed or ineffective via other administration routes. In some embodiments where intravenous injection is used for administration a PET tracer to a human subject, the tracer molecules are mixed in a liquid substance, infused into a vein, either peripheral or central, and carried by the circulatory system of the subject to all parts of his/her body. The cells in the target body absorb the tracer molecules and the absorption level depends on their metabolism activities, hence completing the tracer administration process.

In some embodiments of the present disclosure, intravenous administration is less favorable, such as when the target body has fragile or poorly accessible veins or the nature of the target body and/or the PET study prevents the use of intravenous administration. In this situation, other tracer administration routes might be preferable. For example, in some embodiments, inhalation is used to administer gaseous tracers or deliver tracers to the lung or the brain. The term "inhalation" as used herein refers to inhale of the tracer molecules by the target body via the flow of air into an organism. Particularly, inhalation by smoking a substance is a rapid way to deliver tracers to the brain, as the substance travels directly to the brain without being diluted in the systemic circulation. In other embodiment, oral administration of the tracer molecule is used, where tracer molecules are taken by mouth and absorbed in a subject's digestive system. In some embodiments of the present disclosure, oral administration is used to achieve systematic delivery as the tracer molecules can be assimilated into the whole body of the subject. In other embodiments, oral administration is used as a local administration route, such as for delivering the tracer molecules specifically to the subject's gastrointestinal system. For example, in some embodiments, oral administration of PET tracers can provide diagnostic information about the subject's intestine function, as it correlates to the amount of tracer uptake at the intestine.

Without being bound by any theory, in some embodiment, local tracer delivery is preferred when the PET study is to be performed with respect to a particular part of the target body. The term "targeted delivery" as used herein refers to a method of delivering a substance in a manner such that the concentration of the delivered substance is higher in some parts of a target body than the other. Various types of targeted delivery methods can be used, including active and passive targeted delivery through various delivery vehicles. In some embodiments, a delivery vehicle is non-toxic, biocompatible, non-immunogenic and/or capable of escaping defense mechanisms of the target body. In some embodiments, a vehicle is biodegradable. In other embodiments, a vehicle is capable of delivering the administered substance to a particular location within a target body, such as a specific type of cell, tissue or organ in a subject. Further provided below is a non-exclusive list of exemplary embodiments of possible delivery vehicles: liposomes, micelles and dendrimers, biodegradable particles, nanoparticles. In some embodiments, local injection of the tracer to a particular part of the target body is another way to avoid systemic circulation of the tracer in the target body.

PET Detector

In some embodiments, PET imaging modules of the present system contains specifically designed PET detectors that detect the gamma ray signals emitted from the target body. The term "PET detectors" as used herein refers to an electric component or combination of multiple electric components capable of receiving the gamma-ray signal and converting it into a form of signal that can be processed and analyzed by a processor, such as a computer. Particularly in some embodiments, the original gamma ray signal may undergo several rounds of conversions before it is eventually turned into a form workable by a computer. The sequential conversions can be achieved by synergic operations of multiple electric components of the PET detector, or by a single multi-functional component.

For example, in some embodiments, the gamma ray radiation is first converted into the form of visible or invisible light, and then into an analog or digital signal that is to be processed by a computer. Particularly, in some of these embodiments, the PET detector contains a component capable of absorbing gamma-ray radiation and emitting a fraction of the absorbed energy as lower-energy photons of ultraviolet or visible wavelength, and another component is capable of sensing the light signal and converting it into an electrical signal. More particularly, in some of these embodiments, the component responsible for the conversion is a scintillator, such as a scintillation crystal block.

The terms "scintillator" as used herein broadly relates to any material that has the ability to absorb ionizing radiation and to emit a fraction of the absorbed energy as light. For example, a gamma photon incident on the scintillator creates an energetic electron, either by Compton scatter or by photoelectric absorption; as the electron passes through the scintillator, it loses energy and excites other electrons in the process; these excited electrons decay back to their ground state, giving off light as they do so. As such, the scintillator produces a brief pulse of visible or ultraviolet photons corresponding to each gamma photon that interacts with the scintillator material. The intensity of the light pulses is proportional to the gamma energy deposited in the scintillator.

The scintillator to be used in connection with the present system can be made of various types of materials working under different principles, which include but are not limited to organic or inorganic, crystalline or non-crystalline, liquid, gas or solid materials. Preferably, a suitable scintillator material to be used in connection with the present system is of a high density and radiation hardness, capable of a fast operation speed, and has a low production cost. More preferably, a suitable scintillator material provides a short decay time and high light output, thereby capable of reducing a required PET scan time. Further preferably, a suitable scintillator material has a high detection efficiency for gamma-ray radiation, such that the target body, particularly a patient or live animal subject, can be exposed to a shortened scan time and a lowered PET tracer dose, thereby reducing the risk and undesirable side effects to the patient. Further provided below is a non-exhaustive list of exemplary embodiments of suitable scintillator materials: CdWO4, $BaF_2$, CsF, CsI(Na), CsI(Tl), NaI(Tl), $CaF_2$(Eu), lutetium oxyorthosilicate (LSO) crystals; bismuth germinate (BGO) crystals, gadolinium oxyorthosilicate (GSO) crystals, LYSO crystals, and mixed lutetium silicates (MLS) crystals.

In some embodiments, the PET detector contains a separate electric component, namely a photodetector, which senses the light pulses emitted from the scintillator and converts them into a corresponding electrical signal. Exemplary embodiments of a photodetector that can be used in connection with the present system include Photomultiplier Tube (PMT), Avalanche Photodiode (APD), Single-Photon Avalanche Photodiode (SPAD), Silicon Photomultiplier (SiPM), Digital Silicon Photomultiplier (DSiPM). The photodetector that can be used in connection with the present system described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims.

In some embodiments of the present disclosure, photomultiplier tubes (PMTs) that can be used in connection with the present system are a class of vacuum tubes, and more specifically vacuum phototubes that are capable of absorbing energy of light and re-emit the absorbed energy in the form of electrons via photoelectric effect. The term "photoelectric effect" as used herein refers to the phenomenon that metals emit electrons when light shines upon them; electrons emitted in this manner are referred to as photoelectrons. An exemplary embodiment of a PMT that can be used in connection with the present system is provided in Example 2.1. Exemplary advantages of PMTs include enhanced quantum efficiency, improvements in timing performance. Particularly, multichannel and position-sensitive PMTs allow localization of incoming scintillation photons.

The term "avalanche multiplication" as used herein refers to a phenomenon that allows large currents to occur within insulating or semiconducting materials by generating electron-hole pairs within the material. The term "electron-hole" as used herein refers to an area within an atom or atomic lattice where an atom could but does not exist. There are two types of charge carrier in an insulating or semiconducting material, namely, free electrons and electron holes. A fixed electron in a reverse-biased diode may break free due to its thermal energy, creating an electron-hole pair. When there is a voltage gradient in the insulating or semiconducting material, the electron will move towards the positive voltage while the hole moves towards the negative voltage. Under a right circumstance, such as when the voltage is high enough, the free electron may move fast enough to knock other electrons free, creating more free electron-hole pairs, thereby creating more charge carriers in the material and increasing the current. Thus, in a fraction of a nanosecond, the whole material begins to conduct, a phenomenon known as the avalanche breakdown. Accordingly, the voltage at which avalanche breakdown occurs is referred to as the breakdown voltage.

In some embodiments, avalanche photodiodes (APDs) that can be used in connection with the present system are photodetector devices that employ the photoelectric effects and the avalanche multiplication. In some embodiments, the APDs are made of solid-state silicon materials and are capable of creating a high electric field upon the application of a bias voltage close to the breakdown voltage. The field is high enough that photoelectron charges produced via the absorption of light photons in this region may be accelerated sufficiently to trigger an avalanche current, of which the intensity is linearly related to the optical signal intensity. An exemplary embodiment of a PMT that can be used in connection with the present system is provided in Example 2.2. Exemplary advantages of APDs in connection with the present multi-modality imaging system include that an APD can be made into a small and compact structure, such that a PET detector containing APDs can be small as well and integrated relatively easily into the imaging system. This feature of the APDs is particularly advantageous in the embodiments where the PET imaging modality of the present system is provided as a PET insert. Additionally, since APDs are insensitive to magnetic fields, they can function properly even under the strong and alternating magnetic fields of MR imaging and studies. This feature of APDs is particularly advantageous in those embodiments, where PET/MR dual-modality imaging is desired.

In some embodiments, photodetectors that can be used in connection with the present system include Single Photo Avalanche Diode (SPAD). In some embodiments, the SPAD is a compact solid-state silicon device that is capable of detecting low intensity light emitted by scintillators. Like APDs, SPADs exploit the photon-triggered avalanche current due to the impact ionization mechanism. A main difference between SPAD and APD is that SPADs are specifically designed to operate with a reverse-bias voltage well above the breakdown voltage. This kind of operation is sometimes referred to as the Geiger mode, thus the SPAD are sometimes referred to as "Geiger mode Avalanche Photodiode or GAPD." Because of this unstable above-breakdown regime, a single photon can set off a significant avalanche of electrons in SPAD, which gives SPADs a high sensitivity for detecting low intensity light down to single photons. Particularly, in a SPAD, a single photon triggers a current in the mA region that can be reliably counted. An exemplary embodiment of a PMT that can be used in connection with the present system is provided in Example 2.3. Similar to APDs, SPADs are also small and compact in size and insensitive to magnetic field.

In some embodiments, photodetectors that can be used in connection with the present system include Silicon Photomultipliers, multi-pixel photon counters (WPCs) or solid-state photomultipliers (SSPMs). In some embodiments, the SiPM of the present system is a solid-state silicon single photon sensitive device built from a APDs array on a common Si substrate, usually referred to as a cell or a microcell. Each APD in a SiPM operates in the Geiger-mode and each cell responds independently when incident photons interact with said cell. Particularly, in some embodiments, the Geiger-mode cells of the SiPM are connected in parallel through a long interconnect. More particularly, in some embodiments, the resulting output signal is the analog sum of the individual currents of all cells and the amplitude of the output pulse is proportional to the number of photons incident on the surface of the device. An exemplary embodiment of a PMT that can be used in connection with the present system is provided in Example 2.4. Similar to APDs and SPADs, SiPMs are also small and compact in size and insensitive to magnetic field. Other features that make SiPMs advantageous for using in the present multi-modality imaging system include but not limited to their ruggedness, low operating voltage, low power consumption and possibilities for large-scale fabrications.

In some embodiments, photodetectors that can be used in connection with the present system include a Digital Silicon Photomultiplier (DSiPM). In some embodiments, the DSiPM of the present system is a solid-state silicon based device, which converts photon detection to digital pulses. Particularly, in some embodiments, a DSiPM integrates low-power CMOS electronics into a silicon photomultiplier chip, and converts the detection of each photon directly into an ultra-high-speed digital pulse. This pulse can be directly counted by a on-chip counter circuitry. Particularly, in some embodiments, the DSiPM is based on SPADs integrated in a standard CMOS process. More particularly, photons are detected directly by sensing the voltage at the SPAD anode using a dedicated cell electronics block next to each diode. More particularly, in some embodiments, a DSiPM microcells contains an array of SPADs, each capable of detecting single photons. In some embodiments, unlike analog SiPM, each cell of DSiPM is capable of detecting and storing exactly one photon. An exemplary embodiment of a PMT that can be used in connection with the present system is provided in Example 2.5.

A PET detector may contain one or more PET detection blocks. A PET detection block can receive gamma radiation and convert the received signal into a corresponding electric signal. In some embodiments, A PET detection block contains a set of coupled scintillator and photodetector. For example, in some embodiments, a detection block includes a scintillator crystal block that is optically coupled through a light guide to a photodetector unit or an array of photodetector units. A photodetector unit may be optically coupled to more than one scintillator crystal, or alternatively may be coupled in a one-to-one scintillator to photodetector arrangement. Particularly, in a one-to-one coupling configuration, one photodetector unit is coupled to one scintillation crystal. To collect the maximum amount of light from the scintillator, the photodetector unit can have the same surface area as the scintillator crystal to which it is coupled. Each photodetector unit is electrically connected to a voltage source, while multiple photodetector units may share a single voltage source. The photodetector unit can be a PMT, an APD, a SAPD, a SiPM, or a DSiPM. The photodetector unit used in connection with the present disclosure described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims.

Coupling between the scintillator and photodetector can be made directly or indirectly. For example, in some embodiments, coupling between the scintillator and the photodetector is made indirectly through the use of a photo connector, such as optical fibers, which offers some flexibility to positional arrangements of the different components. (See Example 2.7.) Alternatively, in other embodiments, the electric component responsible for the light-to-electrical signal conversion is directly coupled to the scintillator. For example, in some embodiments, one or more photodetectors are directly attached to at least one surface of a scintillation crystal block. (See Example 2.6) In other embodiments, one or more photodetectors are connected to the surface of a scintillation crystal block via a light transmitting material, such as optical glue, immersion oil or optical coupling materials. The coupling configuration and coupling materials that can be used in connection with the present disclosure described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims.

The coupling material is capable of passing scintillation light onto the photodetector at a high efficiency. Particularly, in some embodiments, the coupling material is chosen such that it has a high transmittance for the emission region of the scintillator. In some embodiments, the coupling material has a refractive index that matches the substrates so as to minimize reflection losses.

Figure 11:
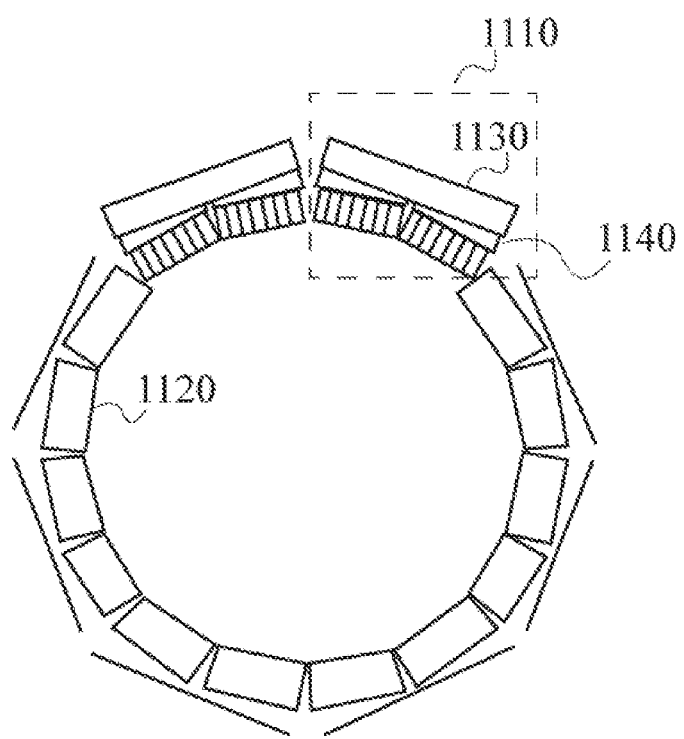
FIG. 11 illustrates an exemplary embodiment of a PET detector having a barrel-shaped configuration according to one embodiment of the present disclosure.
Figure 13:
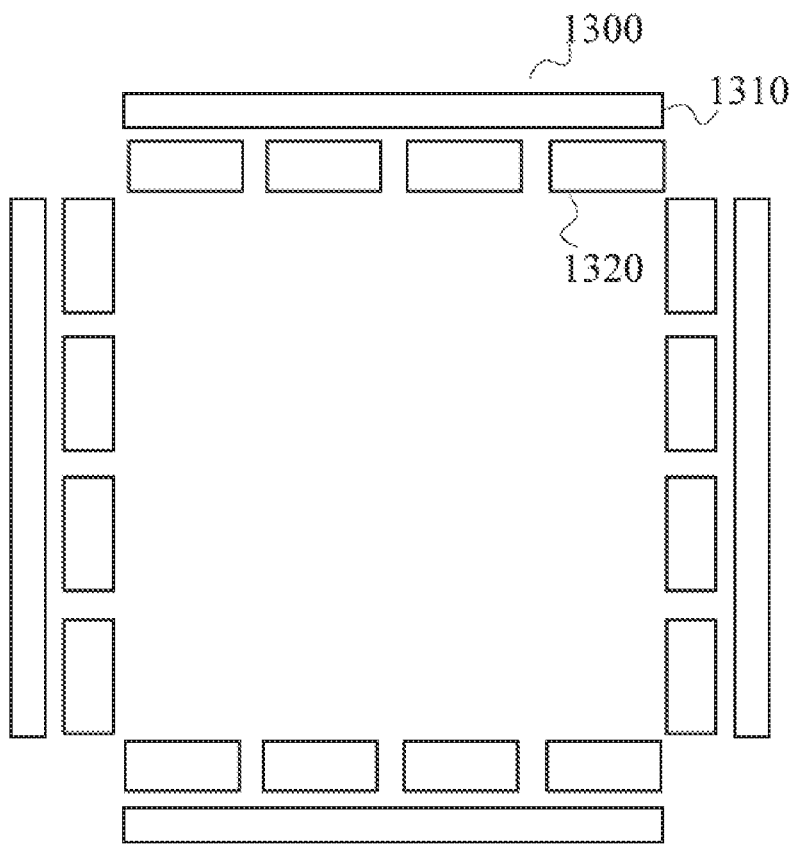
FIG. 13 illustrates an exemplary embodiment of a PET detector having a cubic column configuration according to one embodiment of the present disclosure.

A PET detector thus can have a plurality of detection blocks arranged in different configurations. In some embodiments, a PET detector can have a pair of detection blocks, the scintillator faces of the pair of detection blocks opposing one another. In other embodiments, a PET detector can have multiple pairs of detection blocks, each pair of detection block flanking the sample area with their scintillator faces opposing one another. The plurality detection blocks of a PET detector can form various different configurations, including but not limited to the cubic column configuration as shown in FIG. 13 and the barrel-shaped configuration as shown in FIG. 11. Particularly, as shown in FIG. 13, in the cubic column configuration, four detection blocks form two opposing pairs, each pair flank the sample area thus forming the cubic column; an angle between adjacent detection blocks is 90 degree. As shown in FIG. 11, in the barrel-shaped configuration, eight detection blocks form four opposing pairs, each pair flanks the sample area thus forming the barrel; the eight detection blocks distribute even across a 360-degree circle. Other possible configurations of a PET detector that can be used in connection with the present system are known to those of ordinarily skill in the art.

One or more PET detection blocks may be temporarily removed from the PET detector, such that the target body in the sample area may be exposed and become accessible to the hands or tools of a medial practitioner. Such design thus enables medical practitioner to perform additional examinations, such as manual examination or biopsy, before or after PET imaging, while the target body remains in the same position as during the PET imaging. See Example 4.6.

According to some embodiments of the present disclosure, the PET imaging modality of the present system is specifically designed for imaging a particular portion of a human body, such as the head, a lib, a joint, or an internal organ. Particularly, in some embodiments, the PET imaging modality is suitable for imaging the mammary gland of a female subject or patient.

The term "positron emission mammography" or "PEM" as used herein refers to a particular PET method for imaging positron-emitting isotopes within the mammary gland or breast. In some embodiments, the PEM examines only one of the patient's breasts at a time, while in other embodiments, both breasts are examined at the same time. In some embodiments, the positron-emitting isotopes used for PEM is $^{18}F$ which is delivered to the subject's mammary gland through the administration of the PET tracer compound $^{18}F$-FDG.

For the detection of the PET signal, in some embodiments, a pair of PET detectors are placed on both sides of the subject's breast(s), while in other embodiments, such as those illustrated in Examples 4.1 through Example 4.3, more than one pairs of PET detectors are place around the subject's breast(s). In some embodiments, PEM utilizes a pair of compression paddles that are placed on both sides of the breast to apply a gentle compression on the breast tissue, while in alternative embodiments, no compression is applied and the subject's breast assumes its natural form during the PEM examination. In various embodiments, the subject may lie on the back, the side or in the prone position or sit during the PEM examination.

Local examination of the breasts using PEM overcomes several limitations of whole body PET for detecting breast cancer particularly. First, the local examination using PET detectors that attach closely to the breast tissues avoids the potential difficulty to differentiate breast lesions from other chest wall organs that take up the radiotracer. Further, PEM allows for higher image resolution than regular PET and creates images that are more easily comparable to mammography, because they are acquired in the same position.

Multi-Modality Imaging

According to some embodiments of the present disclosure, components and controls of the different imaging modalities are integrated and capable of both independent and simultaneous operations. Particularly, according to specific needs of an end user, one or more imaging modalities may be chosen to operate on a patient or research subject separately and independently from the rest of the system, producing single-modality images. Alternatively, the end user may choose multiple imaging modalities to operate sequentially or simultaneously with one another, generating sets of multi-modal imaging data. Particularly, in the simultaneous operation mode, scans via multiple imaging modalities can be highly synchronized to produce temporally and spatially co-registered images acquired by different functional and/or anatomical imaging technologies at essentially the same time, thereby obtaining abundant and complementary information of the patient or subject in one short scan.

According to one aspect of the present disclosure, the present imaging system can perform simultaneous multi-modality imaging and analysis. In some embodiments, the simultaneous multi-modality imaging includes PET. Particularly, in some embodiments, the PET imaging module is fully integrated with the other hardware and/or software components of the system, such that the system has a built-in PET function. Alternatively, in other embodiments, the PET function is realized by providing a PET insert. The term "PET insert" as used herein with respect to a multi-modality imaging system broadly refers to a system, sub-system or component for conducting PET imaging and/or analysis, which can be selectively coupled to another system offering at least one imaging modality other than PET, such that upon the coupling, the function and operation of the PET insert is introduced into the other system. The other system is referred to as the "main system" hereinafter.

In some embodiments, the coupling of a PET insert to the main system can be reversible or irreversible. Particularly, in some embodiments of the present disclosure, the PET insert can be installed to the main system when there is a need to perform PET imaging or analysis alone or in combination with particular functions of the main system. For example, in some embodiments, the PET insert is installed such that simultaneous or sequential PET/CT dual-modality scan can be performed; in some embodiments, the PET insert is installed such that simultaneous or sequential PET/MR dual-modality scan can be performed; in some embodiments, the PET insert is installed such that PET/MR/CT tri-modality scan can be performed. Yet, in other embodiments, the PET insert is installed to perform PET studies alone or in various combinations with other types of invasive or non-invasive medical or biomedical procedures, including but not limited to, ultrasound, X-ray, bone densitometry, fluoroscopy and endoscopy. In some embodiments, the PET insert can be uninstalled and removed from the main system after use.

In some of the embodiments where a PET/MR hybrid function is desirable, the PET insert may be installed to a MRI system, a system containing a MRI imaging modality or otherwise offering the MRI function. Particularly, in some of these embodiments, the main system can be a conventional MRI machine that is already commercially available. Exemplary embodiments of a conventional MRI system to be used in connection with the PET insert of the present disclosure include but not limited to the Siemens Magnetom® series MRI scanners, Philips Achieva series MRI scanners, Philips Ingenia series MRI scanners, GE Healthcare SIGNA™ series MRI scanners, Hitachi Echelon series MRI scanners, Toshiba VantageTitan® MRI scanners, Toshiba VantageTitan3T® MRI scanners and Anke OPEN-MARK series MRI scanners, and other commercially available models produced by various manufacturers around the world.

Alternatively, in some embodiments, the main system is a multi-modality system having a built-in MRI imaging modality. Yet, in other embodiments, the main system is a MRI-compatible system, which does not include a complete built-in MR imaging modality, but rather is capable of structurally and functionally integrating a MRI system, sub-system or component for conducting MR imaging and studies.

In some embodiments, the PET insert contains imaging modules for conducting PET imaging, such as the PET detectors. In some embodiments, the PET insert contains its own independent power supply, while in alternative embodiments, the PET insert would use the main system's power supply upon integration. In some embodiments, the PET insert contains its own independent control system and user interface, while in alternative embodiments, the PET insert would operate with the control system and user interface of the main system upon integration. In some embodiments, supporting software of the PET insert is provided as a software plug-in or an update package that can be installed into the main system, while in alternative embodiments, the main system is pre-loaded with the supporting software for the PET insert such that no software installation or upgrade is needed for the integration of the PET insert.

An advantage of the PET insert is that it can be installed into the main system without significantly modify the existing structure, function or operation of the main system. For example, in some embodiments, hardware components of the PET insert can be installed onto existing hardware components of the main system. Example 4.6 illustrates an exemplary embodiment where PET detectors are integrated with a chest support of the patient bed of a conventional MRI scanner. Example 4.7 illustrates an exemplary embodiment where the power system and signal transmission channels of the PET insert are integrated with the main system via the main system's spare pins.

The integration of a PET insert into a main system does not compromise the function and performance of either the PET insert or the main system. Particularly, the present system contains various hardware and/or software-based features for minimizing and/or correcting mutual interferences between the PET insert and the main system upon integration.

For example, according to one aspect of the present disclosure, the multi-modality imaging system offers both PET and MR imaging modalities. In these embodiments, the present system includes various features that are designed to minimize mutual interference between the two modalities to ensure stable, high-quality PET and MRI performances. Particularly, the positioning of various hardware components of the PET detector within the MRI's main magnetic field and the radio frequency field may degrade the homogeneity of these fields and cause a loss of image quality of the MR imaging modality. Accordingly, in some embodiments of the present system, the MR imaging modality employs a local coil which is capable of not only transmitting radio frequency energy to excite the target body, but also capable of receiving nuclear magnetic resonance (NMR) signals as the excited magnetic moments in the target body relax to the initial state. More particularly, in these embodiments, the local coil is placed in vicinity to the target body, and the PET detector is arranged in a manner that does not interfere communications, such as the RF transmitting and NMR signal receiving, between the local coil and the target body.

For example, in some embodiments, to minimize the interference PET components may have on the MR magnetic field, the MRI local coil closely surrounds the target body, while the PET detector is placed further away from the target body, such that PET detection can be achieved without placing any PET component between the MRI local coil and the target body. Examples 4.1 through 4.3 provide three different embodiments of possible arrangements of PET detectors and MRI coils for PET/MR dual-modality imaging of the mammary gland of a subject. Particularly, as illustrated in these examples, one or more breast coils closely surround the subject's breast, while components of the PET detector are placed farther away, forming a PET detection field surrounding the breast tissues without interfering communications between the breast tissue and the breast coil. These embodiments are only exemplary and not intended to be limiting, and further embodiments also include those that will become apparent to those of ordinary skill in the art upon consulting the present disclosure.

Additionally, the placement of various PET components within the MR magnetic fields may further interfere with the performance of the MR imaging modality, when the variable MR gradients induce eddy currents in conductive materials of the PET detector, which would in turn distort the effectiveness of the applied gradient field. Accordingly, in some embodiments, the fabrication materials of the PET components to be placed within MR magnetic fields are selected from those that have a suitable magnetic susceptibility as well as electric conductivity. For example, in some embodiments, the fabrication material of the PET components can be a carbon fiber, a nonferromagnetic metal such as copper, epoxy and/or plastic.

The method for minimizing and/or correcting mutual interferences between the PET insert and the main system upon integration described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims such as those described in Peng et al. *Studies of the interactions of an MRI system with the shielding in a combined PET/MRI scanner*. Physics in medicine and biology, 2010, 55(1): 265, which document herein incorporated by reference in their entirety.

On the other hand, there are also various effects of the MR imaging modality on the performance of the PET imaging modality. For example, the high magnetic field used in MRI may severely impair the function and performance of PET detectors.

According to some embodiments of the present disclosure, the PET imaging components are placed within a shielding enclosure that prevents them from being influenced by MR magnetic fields. Materials that are suitable for making the magnetic shield is known in the art, for example as disclosed in U.S. Pat. No. 8,013,607, which document is herein incorporated by reference in its entirety.

PET components may be thermally sensitive and change their signal gain and characteristics with temperature fluctuations of the individual components. These changes caused by thermal variance can result in a degradation of image quality if not properly monitored and accounted for in the signal acquisition path. Accordingly, in some embodiments, the present system includes a temperature control mechanism to provide a static temperature environment for some thermal-sensitive PET components to work properly. Particularly, in some embodiments, the system includes a water-cooling and/or air-cooling mechanism that removes heat from PET electronics. In some embodiments, the temperature of the amplifiers and photodiodes can be controlled globally by supplying cool air.

PET Data Processing and Image Reconstruction

For PET imaging, a PET tracer is administered to the target body. After the administered tracer reaches a suitable distribution and/or concentration within the target body, data acquisition may begin. Particularly, during imaging, the target body is placed within the sample area surrounded by a number of PET detection blocks of a PET detector. The detection blocks are capable of registering incident gamma rays. As the radionuclide in the PET tracer molecule decays, the resulting positrons subsequently annihilate on contact with electrons in the nearby environment in the target body. Each annihilation produces two 511 keV photons that travel in opposite directions and become detected by the surrounding detection blocks. Two detection events that unambiguously occur within a certain time window are recognized by the PET detector to be coincident, and thus are determined to have come from the same annihilation. These coincidence events can be stored in arrays corresponding to projections through the target body and reconstructed using tomographic technologies. The resulting images show the tracer distribution throughout the target body.

Various PET imaging reconstruction algorithms can be used in connection with the present system. Reconstruction algorithms are known in the art, including but not limited to the OSEM algorithm, FBP algorithm, MLAA algorithm, and PSF algorithm as described in Example 5. The algorithms for PET imaging reconstruction that can be used in connection with the present disclosure described above are not exhaustive and are not limiting, numerous other changes, substitutions, variations, alterations, and modifications may be ascertained to one skilled in the art and it is intended that the present disclosure encompass all such changes, substitutions, variations, alterations, and modifications as falling within the scope of the appended claims such as those described in Bailey et al. *Positron Emission Tomography*. (978-1-85233-798-8) pp. 63-91; Hudson et al. *Accelerated image reconstruction using ordered subsets of projection data*. Medical Imaging, IEEE Transactions on, 1994, 13(4): 601-609; Rezaei et al. *Simultaneous reconstruction of activity and attenuation in time-of-flight PET*. Medical Imaging, IEEE Transactions on, 2012, 31(12): 2224-2233; and Rahmim et al. *Resolution modeling in PET imaging: theory, practice, benefits, and pitfalls*. Medical physics, 2013, 40(6): 064301, which documents are herein incorporated by reference in their entirety.

In some embodiments of the present disclosure, before PET image reconstruction, raw data recorded during a PET scan undergo various modifications and/or corrections. Particularly, two important interactions which photons resulting from positron annihilation undergo before they reach the PET detector are Compton scatter and photoelectric absorption. In Compton scatter, a photon interacts with an electron in the absorber material. In the process, the kinetic energy of the electron is increased, and the direction of the photon is changed. In photoelectric absorption a photon is absorbed by an atom and in the process an electron is ejected from one of its bound shells.

Thus, energy of the annihilation protons may be reduced as they travel through the environment, a phenomenon known as photon attenuation. The total probability that a photon of a particular energy will undergo some kind of interaction with matter when travelling unit distance through a particular substance is called the linear attenuation coefficient of that substance. During PET imaging, annihilation photon attenuation may be caused by photoelectric interactions that happen within the target body or in the nearby environment. For example, in a PET/MR hybrid system, additional photon attenuation may be caused by MRI components, such as coils, located between the target body and the PET detector. Thus, without any attenuation correction, considerable regionally varying errors could occur in the reconstructed PET images, depending on the spatial distribution of substances with different attenuation properties either in or nearby the target body.

Accordingly, in some embodiments of the present disclosure, PET data are corrected for photon attenuation. Various methods for attenuation correction that are known in the art can be used in connection with the present system. Particularly, in some embodiments, a map showing attenuation properties of the target body and/or its surrounding environment is constructed and projected to correct photon attenuation in the reconstructed PET image.

In some embodiments, attenuation properties of the target body and/or other substances in the surrounding sample area (such as RF coils) are probed by moving a known positron-emitting rod source on one side the target body placed in the sampling area, and detecting gamma photons on the other side, thereby generating the attenuation map.

In some embodiments, an attenuation map is constructed based on imaging information generated by a different imaging modality of the multi-modality imaging system, such as MRI and/or CT.

Particularly, in those embodiments where MRI information is used, the method transforms MR imaging information, which relates to proton density in the target body, into attenuation factors for gamma photons, thereby generating the attenuation map. In other embodiments, the method segments the target body into tissue classes based on the MRI information, and assign a uniform linear attenuation efficiency to each class. In other embodiments, the method deforms an attenuation atlas template to morph it to the target body's MR image, thereby obtaining the attenuation map. In other embodiments, the method learns a mapping function to predict continuous attenuation maps based on the MR data. Yet, in other embodiments, the method exploits PET emission data and anatomical information from the MR images to compute an attenuation map. Other methods for MR-based PET attenuation correction include those known to one of ordinary skill in the art, such as described in Bai et al. *Magnetic resonance-guided positron emission tomography image reconstruction*. Seminars in nuclear medicine. W B Saunders, 2013, 43(1): 30-44; and Wagenknecht et al. *MRI for attenuation correction in PET: methods and challenges*, MAGMA. 2013 February; 26(1): 99-113, which documents are herein incorporated by reference in their entirety.

In some embodiments, PET data are corrected for scatter events occurring before the photos reach the PET detector. Various methods for scatter correction that are known in the art can be used in connection with the present system, such as those described in Chinese Patent Application Publication No. CN 201310007126, Watson C C. *New, faster, image-based scatter correction for 3D PET*. Nuclear Science, IEEE Transactions on, 2000, 47(4): 1587-1594, and Levin et al. *A Monte Carlo correction for the effect of Compton scattering in 3-D PET brain imaging*. Nuclear Science, IEEE Transactions on, 1995, 42(4): 1181-1185, which documents are incorporated herein by reference in its entirety.

In a PET detector, performance of various detection blocks may vary, resulting in non-uniformity in their response and/or sensitivity. Such non-uniformity may be caused by the PET detector's geometry, non-uniformity in scintillator crystal's property, gain variations of photodetectors, etc. Accordingly, in some embodiments, variance in performance of different detection blocks of a PET detector is normalized before PET imaging.

Particularly, in some embodiments, a process known as rotating rod normalization can be used. In this process, a radioactive positron-emitting rod (line) source is rotated inside the assembly of a PET detector. The responses for all system lines of response (LORs) are measured. Events measured in the LORs are then used to calculate normalization factors. The normalization factors are then taken into consideration by the system such that all system LORs can be equalized in their response to a true coincidence event.

In some embodiments, a method known as efficiency normalization can be used. The method is used to correct sonogram data prior to image reconstruction. In some embodiments, the efficiency normalization is accomplished through direct normalization techniques, where a special geometry phantom object (such as a cylinder, a rotating plane source, or a rotating line source) is scanned to obtain sonogram data. The sonogram data is then inverted to calibrate a normalization factor, after removing known effects of source geometry, attenuation, random and scatter. In some embodiments, the efficiency normalization is accomplished through component efficiency normalization techniques, which comprises detector geometry factors and crystal efficiency factors. Particularly, detector geometry factors comprise circular detector geometry and solid angle, gamma ray incident angle and crystal depth of interaction. Particularly, crystal efficiency factors comprise intrinsic efficiency and dead time effect. See Theodorakis L, et al. *A review of PET normalization: striving for count rate uniformity*. Nuclear medicine communications, 2013, 34(11): 1033-1045, which document is herein incorporated by reference in its entirety.

In some embodiments, depth-of-interaction (DOI) information of photons in scintillator crystals is taken into consideration during PET imaging. Various known DOI methods known in the art can be used in connection with the present disclosure, such as those described in Miyaoka et al. *Design of a depth of interaction (DOI) PET detector module*. Nuclear Science, IEEE Transactions on, 1998, 45(3): 1069-1073; Ito et al. *Positron emission tomography (PET) detectors with depth-of-interaction (DOI) capability*. Biomedical Engineering Letters, 2011, 1(2): 70-81, which documents are herein incorporated by reference in their entirety.

EXAMPLES

The following examples are for illustrative proposes only and should not be interpreted as limitations of the claimed invention. There are a variety of alternative techniques and procedures available to those of ordinary skill in the art which would similarly permit one to successfully perform the intended invention.

Exemplary Embodiments of Multi-Channel Coils

As described above, the local coil of the MRI imaging modules of the present system may have different architecture and geometry. Several exemplary embodiments are provided below.

Example 1.1—Birdcage Coil

Particularly, FIG. 1 illustrates a specific embodiment of the local coil which comprises a birdcage coil. Particularly, FIG. 1 is a perspective view of the local coil (100). More particularly, the birdcage coil illustrated in this particular embodiment is a multi-channel coil capable of transmitting and receiving radiofrequency. As shown in the figure, the birdcage coil comprises two end-rings (110 and 120) connected by a series of parallel conductors (130). In the end-rings and between the each pairs of conductors locates a circuit component (140). For convenience the circuit components (140) are merely illustrated as a gap between the conductors where the components are located. In various embodiments, circuit components (140) may also be present in the conductors. In alternative embodiments, the circuit components (140) may be present in the conductors only. The birdcage coil (100) is coupled to one or more external switch (not shown in the figure) to operatively switch between the transmit and receive mode.

During imaging, the target body, such as the breast of a female patient, is placed within the hollow space of the birdcage coil (100) for MRI scans. Particularly, the birdcage coil (100) is switched to the transmit mode and generates radiofrequency (RF) energy to excite protons in the target body. Subsequently, the birdcage coil (100) is switched to the receive mode and then picks up nuclear magnetic resonance (NMR) signals as the excited proton spins relax.

In various embodiments, the birdcage coil assumes various configurations. The birdcage coil (100) may be cylindrical, in which case the end-rings (110 and 120) are of the same diameter. The birdcage coil (100) may be conical, in which case the end-rings (110 and 120) are of different diameters. The birdcage coil (100) may be barrel shaped, in which case the end-rings (110 and 120) are of the same diameter, while the conductors (130) are arched.

Example 1.2—Assembly of Birdcage-Transmitting and Phased Array Receiving Coils

Figure 2A:
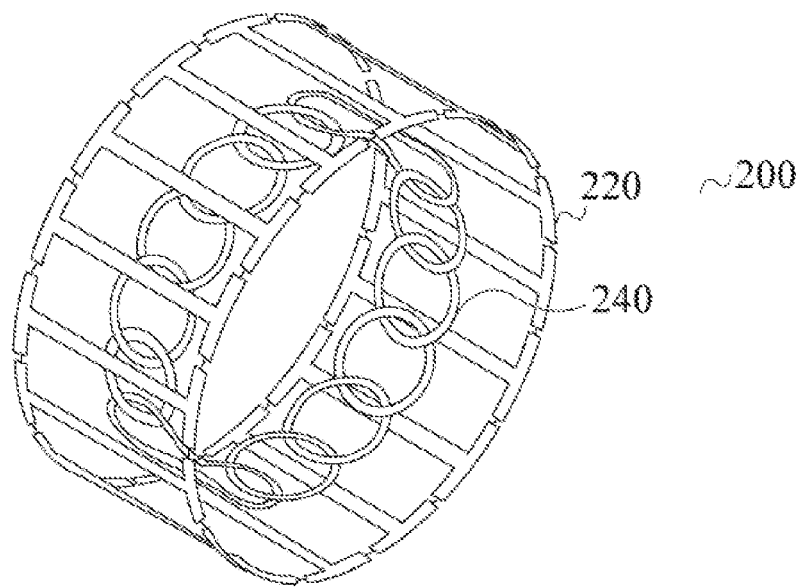
FIG. 2A is a perspective view of an assembly of a birdcage coil and a pseudo-chain-link coil according to one embodiment of the present disclosure.
Figure 2B:
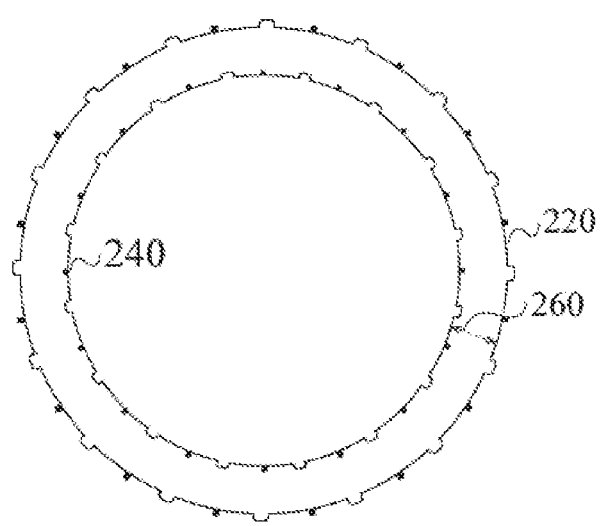
FIG. 2B is a top view of the assembly of the birdcage coil and the pseudo-chain-link coil as shown in FIG. 2A.

Particularly, FIGS. 2A through 2B illustrates a specific embodiment of the local coil which is a coil assembly containing a transmit-only birdcage coil and a receive-only multi-channel phased array coil. Particularly, FIG. 2A is a perspective view of the coil assembly (200). As shown in the figure, the coil assembly (200) includes a receive-only multi-channel phased array coil (240), which contains a plurality of ring shaped coils connected to each other in a pseudo-chain-link configuration and forming a complete circle. The coil assembly (200) further includes a transmit-only 16-channel birdcage coil (220).

FIG. 2B is a vertical view of a cross section of the coil assembly (200) as shown in FIG. 2A. As can be seen from the figure, the coil assembly (200) assumes a barrel shape with a hollow space in the center. The target body, such as the breast of a female patient, is placed within the hollow space for MRI scans. Particularly, during MRI scans, radiofrequency (RF) energy is generated by the transmit-only coil (220) and excites protons in the target body. Subsequently, power supply of the transmit-only coil (220) is turned off using an external switching circuit, and the receive-only phased array coil (240) then picks up nuclear magnetic resonance (NMR) signals as the excited proton spins relax.

As shown in FIG. 2B, the transmit only coil (220) and the receive-only phased array coil (240) are separate from each other, with the receive-only phase array coil (240) disposed coaxially with and inside the transmit-only coil (220). The distance between the coils (220, 240), namely the effective range (260), is carefully designed to minimize a mutual inductance effect between the coils (220, 240).

Example 1.3—Stacked Loop Embodiment

Figure 3:
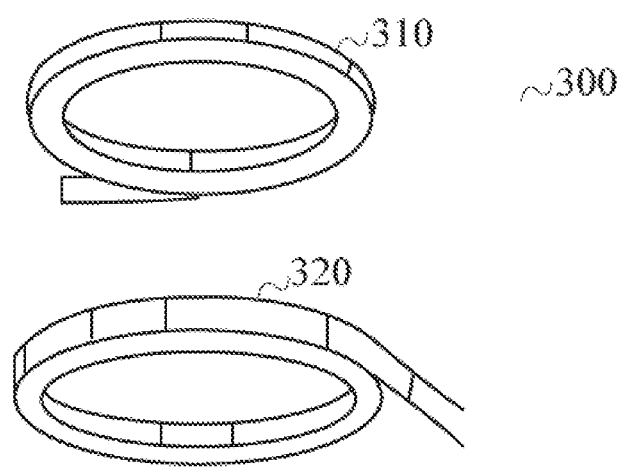
FIG. 3 is a perspective view of a stacked-loop coil according to one embodiment of the present disclosure.

Particularly, FIG. 3 illustrates a specific embodiment of the local coil, which comprises a stacked loop shaped coil (300). Particularly, in this specific embodiment, the stacked loop shaped coil (300) assumes a 2-loop configuration. More particularly, the stacked loop shaped coil (300) is a multi-channel coil capable of transmitting and receiving radiofrequency energy.

As shown in the figure, the stacked loop shaped coil (300) comprises two loops (310 and 320). In other embodiments, the stacked loop shaped coil (300) may comprise one or multiple loops. When oriented at appropriate angles to the main magnetic field, the stacked loop shaped coil (300) may generate a magnetic field by driving an alternating current through its loops (310 and 320). Particularly, the alternating current may be a sinusoidal alternating current.

In various embodiments, the stacked loop shaped coil assumes various configurations. The stacked loop shaped coil may comprise a single loop or multi loops.

Exemplary Embodiments of PET Detectors

Example 2.1—Photomultiplier Tube

Figure 4:
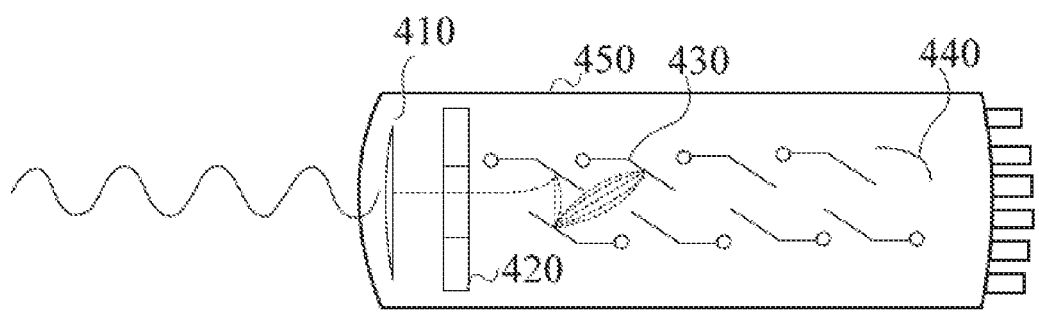
FIG. 4 is a schematic illustration of a photomultiplier tube that may be used in connection with the present system according to one embodiment of the present disclosure.

Particularly, FIG. 4 shows a cross-section view of a specific embodiment of a photomultiplier tube (PMT). As shown in the figure, the PMT comprises a photocathode (410), a focusing electrode (420), an anode (440) and a number of dynodes (430) inside a vacuum phototube (450).

In this embodiment, the photocathode (410) is a negatively charged electrode that is coated with a photosensitive compound that is sensitive to ultraviolet, visible and near-infrared ranges of electromagnetic spectrum. When struck by photons, the photocathode (410) absorbs the energy of photons and emits electrons through photoelectric effect. The emitted electrons are then directed by the focusing electrode (420), which provides an electric field to accelerate the electrons towards the dynodes (430) and the anode (440), where electrons are multiplied by the process of secondary emission.

The dynodes (430) are positive electrodes arranged inside the vacuum phototube (450) in a series, with each dynode (430) held at a more positive potential than the dynode (430) before it. A primary electron leaves the photocathode (410) and is accelerated towards the first dynode (430) by elevated kinetic energy imparted by the potential difference. Upon striking the first dynode (430), more low energy electrons are emitted, and these electrons are then accelerated toward the second dynode (430). After several rounds of multiplication, a large number of electrons reach the anode (440), resulting in a sharp current pulse that is easily detectable.

Example 2.2—Avalanche Photodiode

Figure 5:
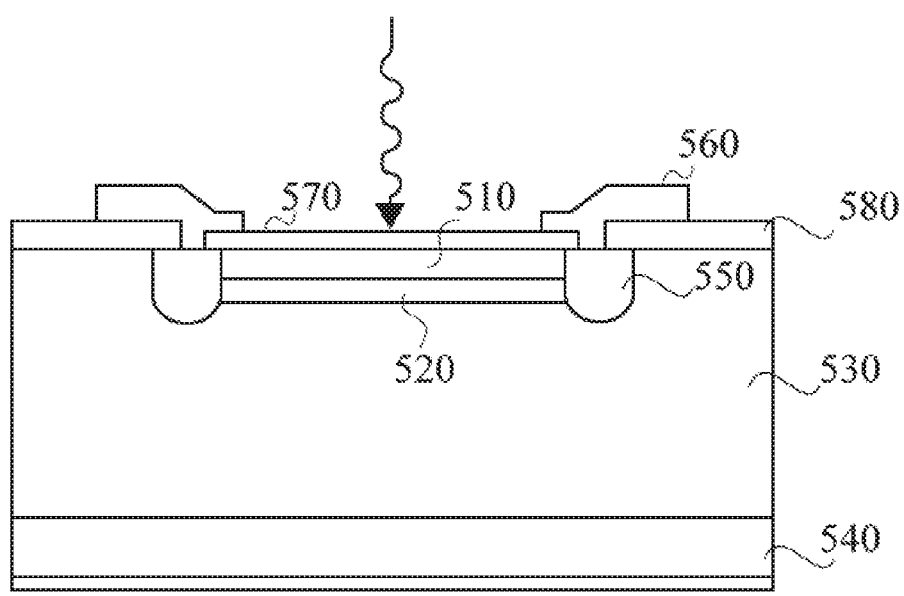
FIG. 5 is a schematic illustration of an avalanche photodiode that may be used in connection with the present system according to one embodiment of the present disclosure.

Particularly, FIG. 5 shows a cross-section view of a specific embodiment of an avalanche photodiode (APD). As shown in the figure, the APD comprises a p-n junction. More specifically, the APD comprises an n-type region (510), a p-type region (520), an intrinsic region (530) and another p-type region (540). The n-type region (510), p-type region (520), intrinsic region (530) and another p-type region (540) form the active region of the APD.

During imaging, a large reverse voltage, typically close to the breakdown voltage of the APD, is applied to the active region of APD. The reverse voltage causes the electrons initially generated by the incident photons to accelerate as they move through the APD active region. As the electrons collide with other electrons in the semiconductor material, they cause a fraction of them to become part of a photocurrent, which is known as avalanche multiplication. Avalanche multiplication continues to occur until the electrons move out of the active area of the APD and form a detectable current of which the intensity is linearly proportional to the intensity of the photon.

In some embodiments, the APD further comprises guard rings (550) around the perimeter of the diode junction to prevent surface breakdown mechanisms. In some embodiments, the APD further comprises electrical contacts (560) at the side of the device to ensure that the maximum amount of light reaches the intrinsic layer. In some embodiments, the APD further comprises antireflective coating (570) at the surface of the APD to eliminate light reflection. The APD further comprises insulator regions (580) at the side of the junction.

Example 2.3 Single-Photon APD

Figure 6:
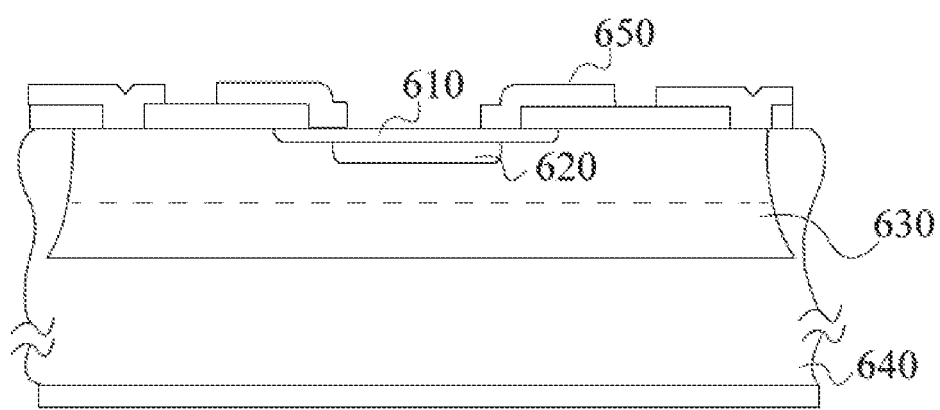
FIG. 6 is a schematic illustration of a single-photon photodiode that may be used in connection with the present system according to one embodiment of the present disclosure.

Particularly, FIG. 6 shows a cross-section view of a specific embodiment of a single photon avalanche diode (SPAD). As shown in the figure, the SPAD comprises a p-n junction. More specifically, the SPAD comprises an n-type region (610), a p-type region (620), an intrinsic region (630) and another p-type region (640). The n-type region (610), p-type region (620), intrinsic region (630) and another p-type region (640) form the active region of the SPAD.

Similar to APDs, the SPADs exploit the photon-triggered avalanche current of a reverse biased p-n junction to detect an incident photon. The major difference between SPAD and APD is that the reverse voltage applied to SPADs is well above the breakdown voltage of SPADs and thus a single photon can trigger an avalanche current that is easily detectable. Therefore, the multiplication of the avalanche current is not linearly proportional to the intensity of intrinsic photons.

Example 2.4—Silicon Photomultiplie

Figure 7:
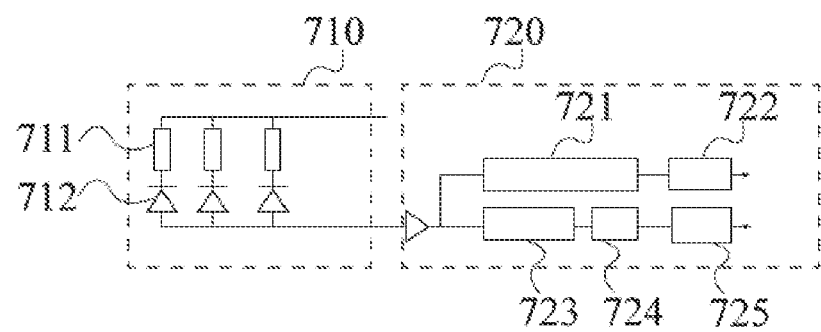
FIG. 7 is a schematic illustration of a silicon photomultiplier and its corresponding circuit that may be used in connection with the present system according to one embodiment of the present disclosure.

Particularly, FIG. 7 illustrates a schematic view of a specific embodiment of a silicon photomultiplier (SiPM). As shown in the figure, the SiPM comprises two major components, a series of microcells (710) on a solid-state substrate and corresponding readout application-specific integrated circuit (ASIC) (720). The microcells (710) comprises a series of photodiodes (712) in connection with their respective quenching resistors (711). Particularly, the photodiodes (712) used in the SiPM can be a SPAD. As shown in the figure, the photodiodes (712) are connected in parallel through interconnects, and the reverse biased voltage is applied to the array of the photodiodes (712) during imaging. When struck by incident photons, each photodiode (712) responds to photon detection and generates charge pulse. The sum of the charge pulse generated by the array of photodiodes (712) is fed to the readout ASIC (720).

The readout ASIC comprises two logic blocks to record the timestamp of a photon detection and the energy. Particularly, the readout ASIC comprises multiple electric components including a discriminator (721) in connection with a time-to-digital converter (TDC) (722) to record the timing, and a sharper (723) in connection with another discriminator (724) and an analog-to-digital converter (ADC) (725) to record the energy. More particularly, the discriminator (721) is a pulse height discriminator that separates the signal pulses from the noise pulses, enabling high-precision measurement with a higher signal-to-noise ratio. The discriminator (721) compares the input voltage pulses with a preset reference voltage or threshold voltage and eliminates those pulses with amplitudes lower than said value. The TDC (722) is used to measure a time interval between each incoming pulse and convert it into digital output. The subsequent processing unit (not shown in the figure) can take advantage of the digital output of time intervals for time of flight calculation.

To quantify the energy of the incident photons, the sum of the charge pulse generated by the array of photodiodes (712) is inputted to shaper (723) for pulse shaping. The term "pulse shaping" as used herein refers to the process of changing the waveform of transmitted pulses. Typically, a pulse shaping process limits the effective bandwidth of the transmission. After pulse shaping, the incoming pulse is filtered by another discriminator (724), and then converted to a digital number that represents its amplitude by the ADC (725). The subsequent processing unit (not shown in the figure) can take advantage of the output of pulse amplitude to analyze the energy of incident photons.

In various embodiments, the electric components used within the ASIC (720) may have different connection arrangements as long as it performs the function indicated above.

Example 2.5—Digital Silicon Photomultiplie

Figure 8:
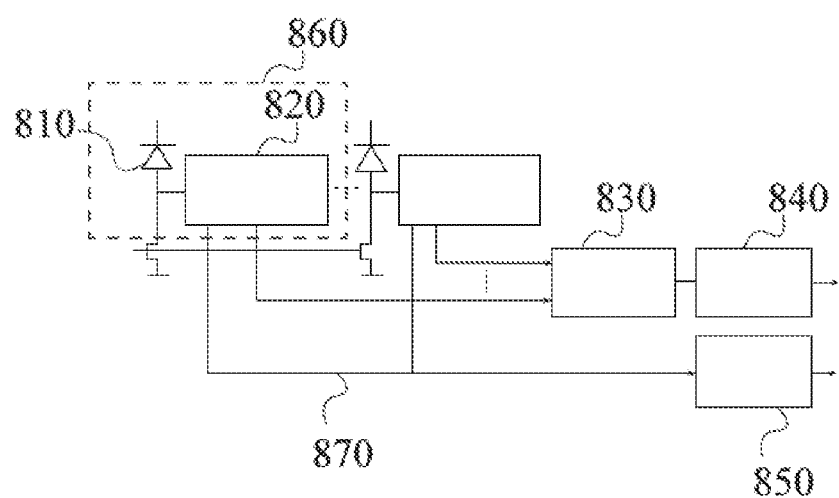
FIG. 8 is a schematic illustration of a digital silicon photomultiplier and its corresponding circuit that may be used in connection with the present system according to one embodiment of the present disclosure.

Particularly, FIG. 8 illustrates a schematic view of a specific embodiment of a digital silicon photomultiplier (DSiPM). As shown in the figure, the DSiPM comprises multiple photodiodes (810) integrated with complementary metal-oxide-semiconductor (CMOS) circuits on the same substrate. Particularly, the photodiodes used in the DSiPM can be a SPAD. Particularly, each photodiode (810) has its own readout circuit (820). Each photodiode (810) and the corresponding circuit (820) form a microcell (860). Each microcell (860) has access to two logic blocks to record the timing and energy of a photon hit.

Particularly, to record the timing, a series of microcells (860) are connected to a trigger network (830). The trigger network (830) is used to propagate the trigger signal from all cells to the integrated time-to-digital converter (TDC) (840). The TDC (840) is used to measure a time interval between each incoming pulse and convert it into digital output. The subsequent processing unit (not shown in the figure) can take advantage of the digital output of time intervals for time of flight calculation.

Particularly, the energy of the photons is done by recording the number of detected photons, i.e. broke-down microcells. A series of the microcells (860) are connected by a synchronous bus (870) to a photon counter (850). The photon counter (850) counts each photon detection and outputs the values as digital signals. The subsequent processing unit (not shown in the figure) can take advantage of the digital outputs to analyze the energy of incident photons.

Example 2.6—Direct Coupling

Figure 9:
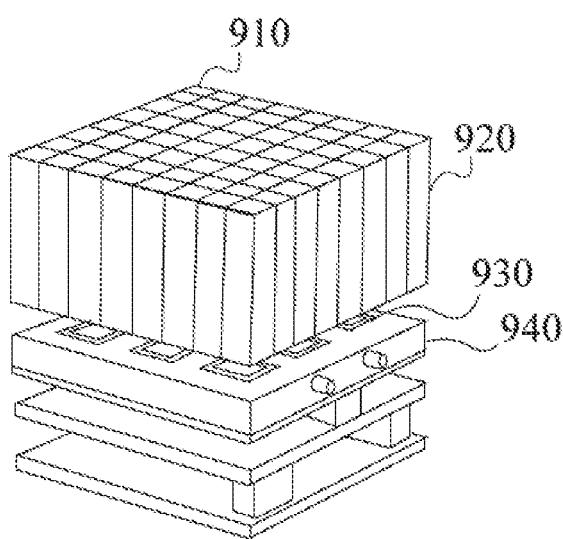
FIG. 9 illustrates an exemplary embodiment of a PET detection block and the direct coupling between the scintillator crystal array and the photodetector of the detection unit.

Particularly, FIG. 9 illustrates a schematic view of the direct coupling between a scintillator and a photodetector. Particularly, the scintillator (920) comprises an array of scintillator crystals (910). More particularly, the scintillator crystals used in this particular embodiment is an array of LSO crystals. The photodetector (940) comprises an array of photodiodes (930). More particularly, the photodiodes used in this particular embodiment is an array of APDs. As shown in the figure, the scintillator (920) is directly coupled to the photodetector (930) without the use of a connector. Particularly, the output of the scintillator (920) is directly coupled to the input surface of the photodetector (930).

Example 2.7—Indirect Coupling

Figure 10:
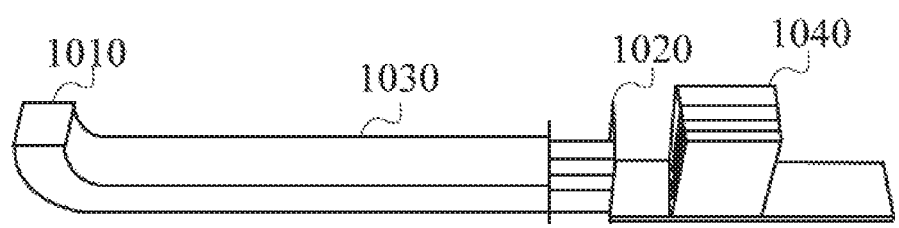
FIG. 10 illustrates an exemplary embodiment of a PET detection block and the indirect coupling between the scintillator and the photodetector via optical fibers.

Particularly, FIG. 10 illustrates a schematic view of the indirect coupling between a scintillator and a photodetector. More particularly, the scintillator (1010) used in this particular embodiment is optically coupled to the photodetector (1020) used in this particular embodiment via optical fiber bundles (1030). More particularly, one end of the optical fiber (1030) is attached to the output of the scintillator (1010), and the other end of the optical fiber (1030) is attached to the input of the photodetector (1020). In various embodiments, the optical fiber bundles (1030) assume various configurations such as length and width. Particularly, the photodetector (1020) used in this particular is an APD. In various embodiments, a preamplifier (1040) is mounted proximal to the APD to amplify the signals. In alternative embodiments, the preamplifier (1040) is optional.

In various embodiment, the scintillator (1010) and the photodetector (1020) is indirectly coupled via light transmitting intermediates such as optical glue, optically coupling material, an immersion oil or other similar coupling materials.

Exemplary Embodiments of PET Detector

Example 3.1—Barrel-Shaped Configuration of a PET Detector

Particularly, FIG. 11 illustrates a schematic view of a PET detector ring used block detectors. As can be seen in the figure, eight PET detector block (1110) forms an octagon which is close to a circular shape. The eight PET detector block (1110) distribute evenly, with each block (1110) facing a separate octant of a 360 degree field. Particularly, there is a hollow space within the octagon for target body during imaging sessions. More particularly, each PET detector block (1110) comprises two scintillator crystals (1120) and one PET photodetector (1130). The scintillator crystal side of the PET detector block (1110) is placed at the inner side of the PET detector ring while the PET photodetector (1130) locates at the outer ring. The scintillator crystals (1120) of the PET detector block (1110) form a hexadecagon with each scintillator crystal locating on one edge of the hexadecagon. More particularly, each pair of the crystals is approximately centrosymmetric about the center of the hexadecagon.

Figure 12:
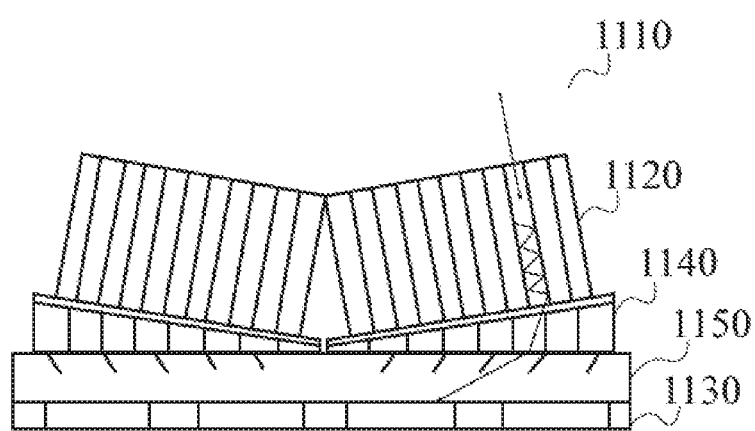
FIG. 12 illustrates a detailed view of PET detector comprising scintillator crystals and photodiodes.

Particularly, FIG. 12 illustrates a detailed view of the PET detector block (1110). As can be seen in the figure, each PET detector block (1110) comprises two scintillator crystal blocks (1120), two angled light guides (1140), a slotted light guide (1150), and a photodetector (1130). Particularly, the two scintillator crystal blocks (1120) are approximately axisymmetric about the middle line perpendicular to the horizontal surface of the photodetector block (1130). In this particular embodiment, the angled light guide (1140) is an optical fiber based light guide capable of transfer the light emitted by the scintillator crystal (1120) to the slotted light guide (1150). The slotted light guide (1150) defines a preselected number of slots. At least one slot is associated with each angled light guide (1140). During imaging, photons exit the angled light guide (1140) and enter the slotted light guide (1150) wherein the photons are distributed with controlled predictability along the length of the slotted light guide (1150). Thus, the photodetector (1130) is capable of detecting the photons at preselected locations along the length of the slotted light guide (1150) and the situs of the photon emitted as a result of the annihilation of the positron can be determined.

Example 3.2—Cubic Column Configuration of a PET Detector

Particularly, FIG. 13 illustrates a top view of PET detector blocks that assume a cubic column shape. Particularly, as can be seen in the figure, each PET detector block (1300) comprises an array of scintillator crystal (1320) and a PET photodetector (1310). Each PET detector block (1300) forms a wall of a cubic column, two PET detector blocks (1300) form a pair, and four PET detector blocks form a cubic column with a hollow space within it. The angle between adjacent blocks (1300) is approximately 90 degree. The side of scintillator crystal arrays of the PET detector block (100) faces toward the hollow space in the center, with the scintillator faces of each pair of opposing blocks (1300) facing each other. The side of PET photodetector (1310) locates at the outer side. During imaging, the target body, e.g. one side of the breast of a female patient, can be placed within the hollow space. In various embodiments, the PET photodetector block (1310) and the scintillator crystals (1320) are directly coupled with each other. In alternative embodiments, the coupling is indirect.

Exemplary Embodiments of PET Insert Integration

Figure 14:
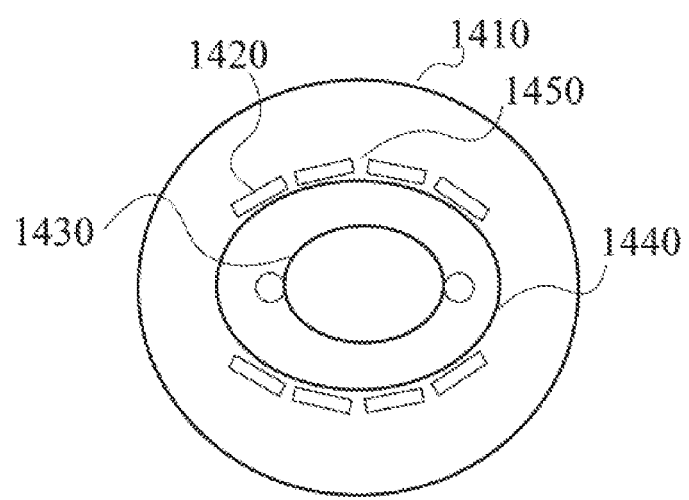
FIG. 14 illustrates an exemplary arrangement of a PET detector, a MRI coil system and a patient's chest in a PET/MR multi-modality imaging system according to one embodiment of the present disclosure. In this exemplary embodiment, the PET detector and the MRI coil surround the entire chest circumference of the patient.

Example 4.1—Exemplary Arrangements of a PET Detector and MRI Coils in a PET Insert FIG. 14 is a schematic illustration of an exemplary embodiment of a PET insert. Particularly, the PET insert includes the assembly of a PET detectors (1450) and a breast coils (1440) for PET/MR dual-modality imaging of one or both breasts of a human subject.

Particularly, as can be seen from the figure, the PET detector (1450) in this particular embodiment assumes an elliptic configuration. Particularly, the PET detector (1450) contains eight PET detection blocks (1420). The eight blocks (1420) form four pairs, the scintillator faces of each pair of opposing blocks (1420) facing each other. In the elliptic configuration, the eight detection blocks (1420) line up along two arcs surrounding the breast coil (1440), thereby forming the PET detector/MRI coil assembly for imaging the mammary gland of the subject. In this particular embodiment, the PET detectors (1450) and the breast coils (1440) can be mounted together or can be mounted on separate supporting structures (not showing in this figure).

As shown in the schematic illustrations of FIG. 14, the PET insert can be integrated with a main system (1410) having MRI function. Particularly, in some embodiments, such as shown in the schematic illustration of FIG. 14, the PET detector (1450) and the breast coil (1440) surround the subject's entire chest circumference. In these embodiments, the subject inserts her upper body through the breast coil (1440), and places her chest within the hollow space surrounded by the PET detector (1450) and the breast coil (1440) during imaging sessions. In alternative embodiments, the PET detector (1450) and the breast coil (1440) only surround the subject's breast tissues. In these embodiments, such as the one illustrated in Example 4.5, during imaging sessions, the subject inserts one or both sides of her breasts into the hollow space surrounded by the PET detector (1450) and the breast coil (1440). As will be further illustrated in Example 4.6, in some embodiments, the PET insert is mounted on a patient support structure of the main system (1410). The patient support then moves the patient and the PET insert to a position relative to the main system (1410) where MR imaging and analysis can be performed. In this particular embodiment, the PET detector (1450) may contain photodetectors of various different designs, such as PMTs, APDs, SPADs, SiPMs or DSiPMs as illustrated in Examples 2.1 through Example 2.5 of the present disclosure. The breast coil (1440) can be a multi-channel coil having various different configurations, such as those illustrated in Examples 1.1 through Example 1.3 of the present disclosure. The breast coil (1440) can both transmit radiofrequency energy to and receive nuclear magnetic resonance (NMR) signal emitted from the subject's breast tissues.

Figure 15:
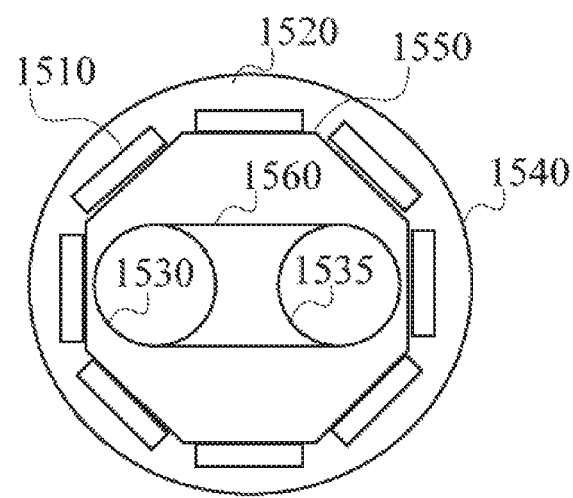
FIG. 15 illustrates an exemplary arrangement of a PET detector and a MRI coil system in a PET/MR multi-imaging system according to one embodiment of the present disclosure. In this exemplary embodiment, the PET detector assumes a barrel-shaped configuration, and the MRI coil system is designed to closely surround both breasts of a subject.

Example 4.2—Exemplary Arrangements of a PET Detector and MRI Coils in a PET Insert FIG. 15 is a schematic illustration of another exemplary embodiment of a PET insert. Particularly, the PET insert includes the assembly of a PET detector (1520) and two breast coils (1530, 1535) for PET/MR dual-modality imaging of one or both sides of breasts of a human subject.

Particularly, as can be seen from the figure, the PET detector (1520) in this particular embodiment assumes the barrel configuration as illustrated in Example 3.1. Particularly, the PET detector (1520) contains eight PET detection blocks (1510). The eight blocks (1510) form four pairs, the scintillator faces of each pair of opposing blocks (1510) facing each other. In the barrel configuration, the eight detection blocks (300) distribute evenly across the circle, with each detection block (1510) facing a separate octant of a 360-degree field. The eight detection blocks (1510) of the PET detector (1520) surround both breast coils (1530, 1535), thereby forming the of PET detector/MRI coil assemblies for imaging one or both sides of breasts. In this particular embodiment, the PET detector (1520) is mounted on the supporting structure (1550), and the breast coils (1530, 1535) are mounted on a separate supporting structure (1560).

As shown in the schematic illustrations of FIG. 15, the PET insert can be integrated with a main system (1540) having MRI function. As will be further illustrated in Example 4.5, when in use, a patient lies in proximity to the PET insert, and inserts her two breasts into the two hollow spaces surrounded by the breast coils (1530,1535), respectively. As such, each breast is surrounded by a breast coil (1530 or 1535) and the eight PET detection blocks (1510) during imaging sessions. As will be further illustrated in Example 4.6, in some embodiments, the PET insert is mounted on a patient support structure of the main system (1540). The patient support then moves the patient and the PET insert to a position relative to the main system (1540) where MR imaging and analysis can be performed. In this particular embodiment, the PET detector (1520) may contain photodetectors of various different designs, such as PMTs, APDs, SPADs, SiPMs or DSiPMs as illustrated in Examples 2.1 through Example 2.5 of the present disclosure. The breast coil (1530 or 1535) can be a multi-channel coil having various different configurations, such as those illustrated in Examples 1.1 through Example 1.3 of the present disclosure. The breast coil (1530 or 1535) can both transmit radiofrequency energy to and receive nuclear magnetic resonance (NMR) signal emitted from the subject's breast tissues.

Figure 16:
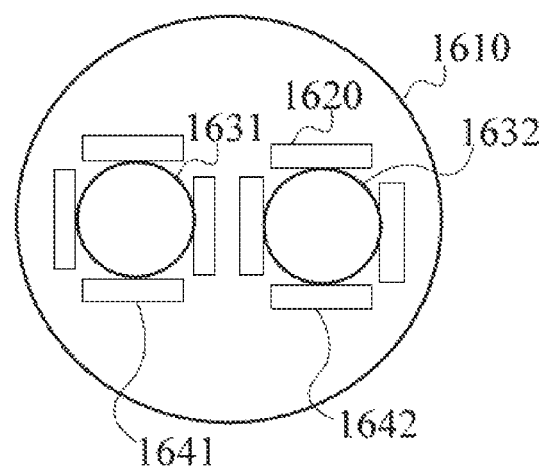
FIG. 16 illustrates an exemplary arrangement of a pair of PET detectors and a pair of MRI coil systems in a PET/MR multi-imaging system according to one embodiment of the present disclosure. In this exemplary embodiment, each PET detector assumes a cubic column configuration, and each MRI coil system is designed to closely surround one breast of a subject.

Example 4.3—Exemplary Arrangements of a PET Detector and MRI Coils in a PET Insert FIG. 16 is a schematic illustration of yet another exemplary embodiment of a PET insert. Particularly, the PET insert includes the assembly of two PET detectors (1641, 1642) and two breast coils (1631, 1632) for PET/MR dual-modality imaging of both sides of breasts of a human subject. Particularly, as can be seen from the figure, both PET detectors (1641, 1642) in this particular embodiment assume the cubic column configuration as illustrated in Example 3.2. Particularly, each PET detector (1641, 1642) contains four PET detection blocks (1620). In the cubic column configuration, the four detection blocks (1620) form two pairs, the scintillator faces of each pair of opposing blocks (1620) facing each other. The angle between adjacent blocks (1620) is approximately 90 degree. The four detection blocks (1620) of the PET detector (1642) surround the breast coil (1632), and the four detection blocks (1620) of the PET detector (1641) surrounds the breast coil (1631), thereby forming two sets of PET detector/MRI coil assemblies for imaging one or both sides of breasts. In this particular embodiment, the PET detectors (1641, 1642) and the breast coils (1631, 1632) can be mounted together or can be mounted on separate supporting structures (not showing in this figure).

As shown in the schematic illustrations of FIG. 16, the PET insert can be integrated with a main system (1610) having MRI function. As will be further illustrated in Example 4.5, when in use, a patient lies in proximity to the PET insert, and inserts her two breasts into the two hollow spaces surrounded by the breast coils (1631,1632), respectively. As such, each breast is surrounded by a breast coil (1631 or 1632) and four PET detection blocks (1620). As will be further illustrated in Example 4.6, in some embodiments, the PET insert is mounted on a patient support structure of the main system (1610). The patient support then moves the patient and the PET insert to a position relative to the main system (1610) where MR imaging and analysis can be performed. In this particular embodiment, the PET detector (1641, 1642) may contain photodetectors of various different designs, such as PMTs, APDs, SPADs, SiPMs or DSiPMs as illustrated in Examples 2.1 through Example 2.5 of the present disclosure. The breast coil (1631, 1632) can be a multi-channel coil having various different configurations, such as those illustrated in Examples 1.1 through Example 1.3 of the present disclosure. The breast coil (1631, 1632) can both transmit radiofrequency energy to and receive nuclear magnetic resonance (NMR) signal emitted from the subject's breast tissues.

Example 4.5—PEM/MR Hybrid System Based on Combined Conventional MRI System and PET Insert FIG. 17 through FIG. 20 illustrate an exemplary embodiment of a PET/MR hybrid system specifically designed for simultaneous PEM-MR dual-modality imaging of a patient's mammary gland.

Figure 17:
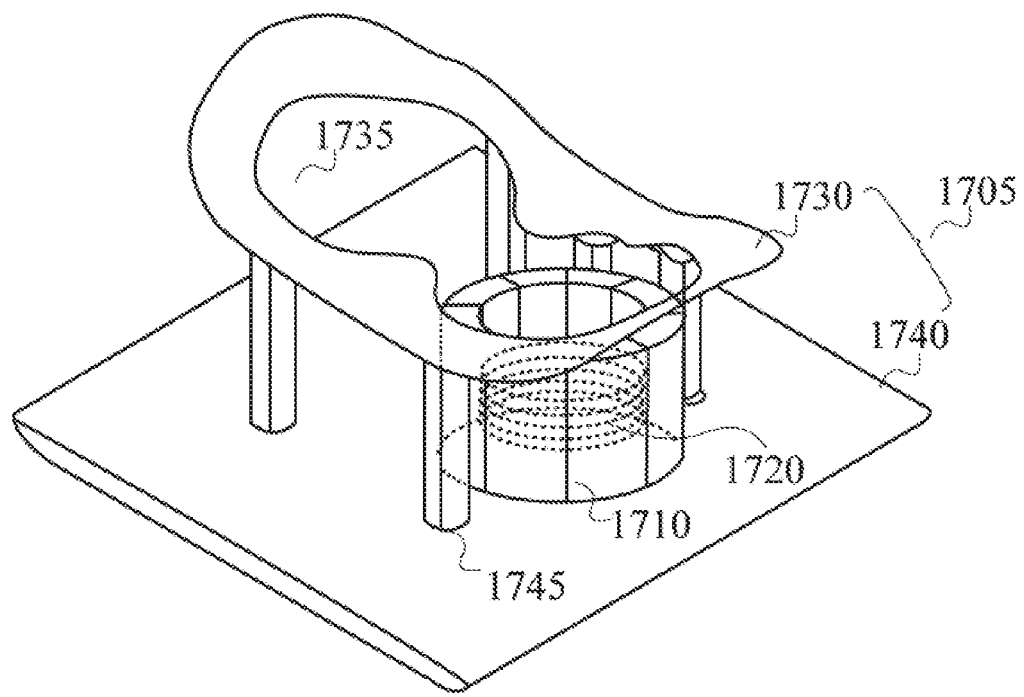
FIG. 17 is a perspective view of an assembly of a PET detector, a MRI coil system and a chest support according to one embodiment of the present disclosure. In this exemplary embodiment, the PET detector and the MRI coil system are placed under an opening of the chest support, such that the patient lying in prone can insert her breast through the opening into the sample area surrounded by the PET detector and the MRI coil system.

Particularly, FIG. 17 is a perspective view showing the exemplary embodiment of an assembly of a PET detector (1710) and a breast coil (1720) mounted on a patient support (1705). In this particular embodiment, there is only one set of the assembly for imaging one breast at a time. Particularly, as can be seen in the figure, in this particular embodiment, the PET detector (1710) has a barrel-shaped configuration and multiple PET-detecting units as illustrated in Example 3.1 of the present disclosure. The breast coil (1720) is a multi-channel coil having the stacked loop configuration as illustrated in Example 1.3 of the present disclosure. The patient support (1705) has a chest support (1730) having an approximate profile of a human patient's front chest with an opening (1735) for inserting the patient's breasts through. The chest support (1730) is mounted on a base (1740) through four supporting legs (1745).

Figure 18:
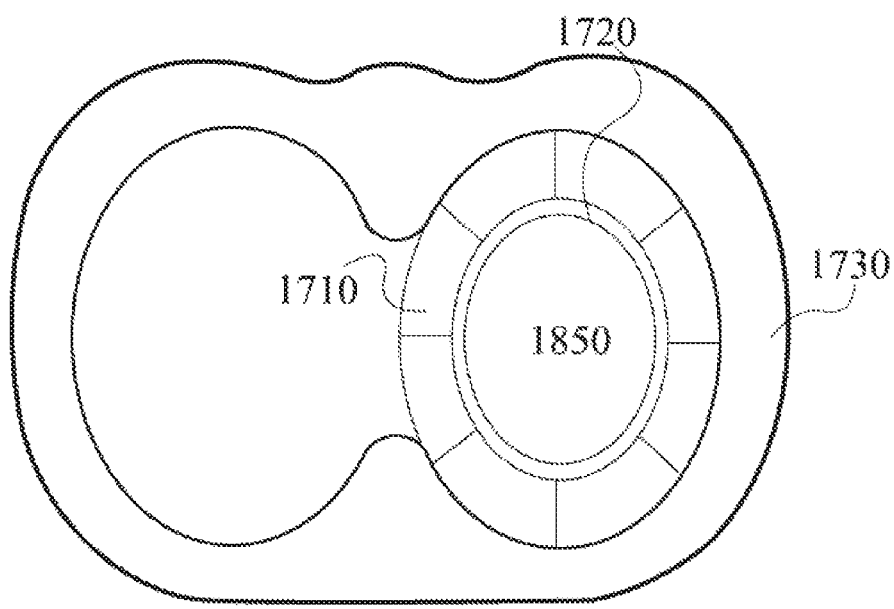
FIG. 18 is a top view of the assembly of a PET detector, a MRI coil system and a chest support as shown in FIG. 17.
Figure 19:
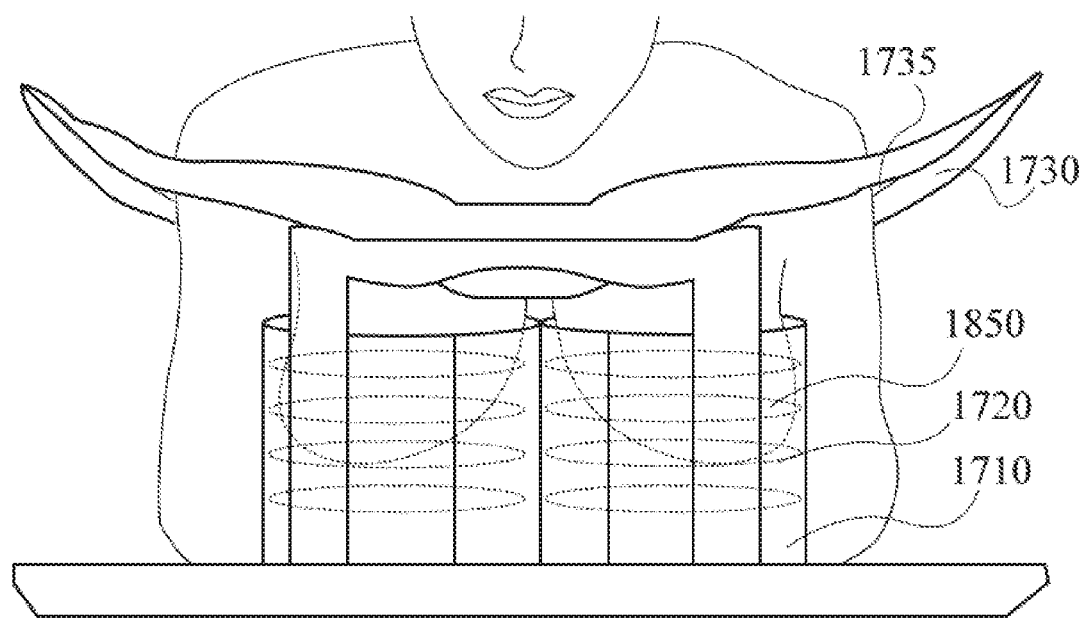
FIG. 19 is a perspective view of a patient lying in prone position with her breast tissue inserted through the opening of the chest support into the assembly of a PET detector and a MRI coil system. In this embodiment, the PET detector assumes a barrel-shaped configuration, and the MRI coil system assumes a stacked-loop configuration.

FIG. 18 is a top view of this particular embodiment. As can be seen in from this figure, the breast coil (1720) having the stacked loop configuration is situated within the barrel-shaped PET detector (1710) in an approximate concentric configuration, thus the assembly of the PET detector (1710)

and the breast coil (1720) form a barrel-like structure with a hollow space (1850) in the center. The assembly of the PET detector (1710) and the breast coil (1720) is placed in between the chest support (1730) and the base (1740) underneath the opening (1735). As shown in FIG. 19, when in use, a patient lies in the prone position on top of the patient support (1705). Particularly, the patient places the chest upon the chest support (1730), and have one or both sides of the breast inserted through the opening (1735) on the chest support (1730) into the hollow space (1850) within the barrel-like assembly of the PET detector (1710) and the breast coil (1720).

In some embodiments, the patient support (1705) can be a hardware component of a MRI imaging modality of an imaging system. For example, in this embodiment, the patient support (1705) can be part of a patient bed of a conventional MRI machine (not shown in the figure), which has an extended area for the patient to lay the whole body flat and moves the patient into the magnetic field area within the MRI machine. In alternative embodiments, the patient support (1705) can be a hardware component of the PET insert, which can be integrated with a MRI system to perform PET-MR hybrid imaging.

Particularly, during the MR imaging, when the patient's breast tissue is in a proper position under the influence of the MRI magnetic fields, the breast coil (1720) first transmits radiofrequency energy to the inserted breast tissue and then receives nuclear magnetic resonance signals emitted from the tissue and transmits the collected signals to a data processing unit (not shown in the figure). Sequentially or simultaneously, the PET detector receives gamma-ray radiation emitted from the same tissue and transmits the signal to a same or different data processing unit (not shown in the figure).

Figure 20:
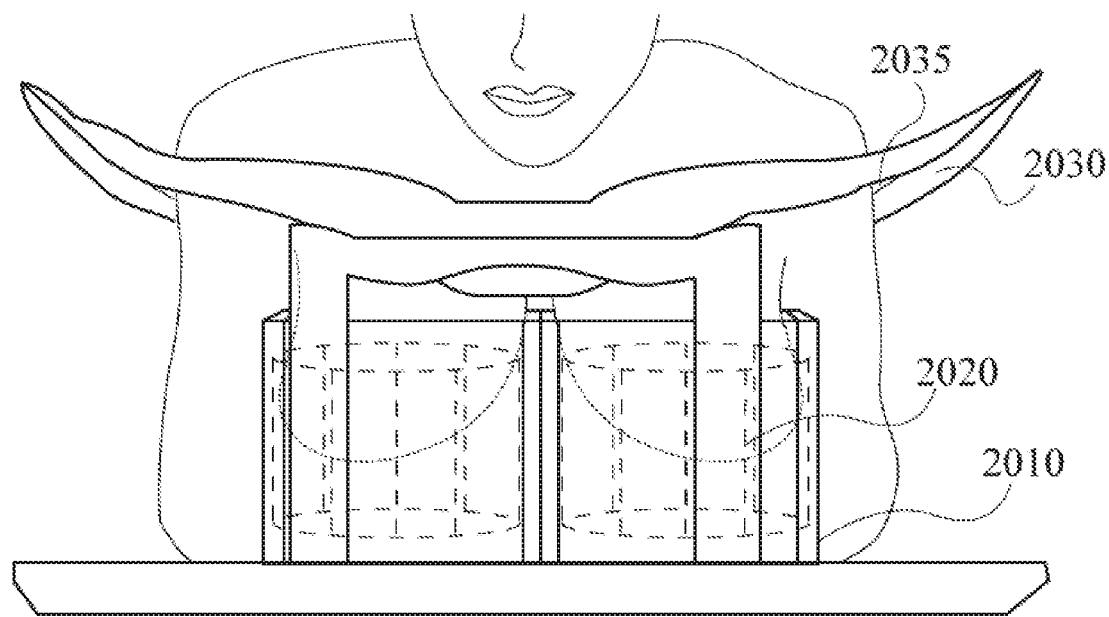
FIG. 20 is a perspective view of a patient lying in prone position with her breast tissue inserted through the opening of the chest support into the assembly of a PET detector and a MRI coil system. In this embodiment, the PET detector assumes a cubic column configuration, and the MRI coil system is a multi-channel birdcage coil.

In alternative embodiments, there can be two sets of the assembly of the PET detector (1710) and breast coil (1720) for examining both sides of the patient's breasts simultaneously. In some embodiments, the PET detector (1710) and the breast coil (1720) can have different configurations from as shown in FIG. 17 through FIG. 19. For example, FIG. 20 illustrates an alternative embodiment of the assembly of the PET detector (2010) and the breast coil (2020). As can be seen from the figure, a female patient lies in the prone position with her left breast inserted into through the opening (2035) of the chest support (2030) into the assembly of the PET detector (2010) and the breast coil (2020) placed under the opening (2035). Particularly, in this embodiment, the PET detector (2010) assumes the cubic column configuration as illustrated in Example 3.2 of the present disclosure. The breast coil (2020) in this embodiment is a multi-channel birdcage coil as illustrated in Example 1.1 of the present disclosure. The birdcage breast coil (2020) is arranged inside the cubic column of the PET detector (2010), and the patient's breast is placed within the hollow space surrounded by the breast coil (2020) and the PET detector (2010).

Figure 21A:
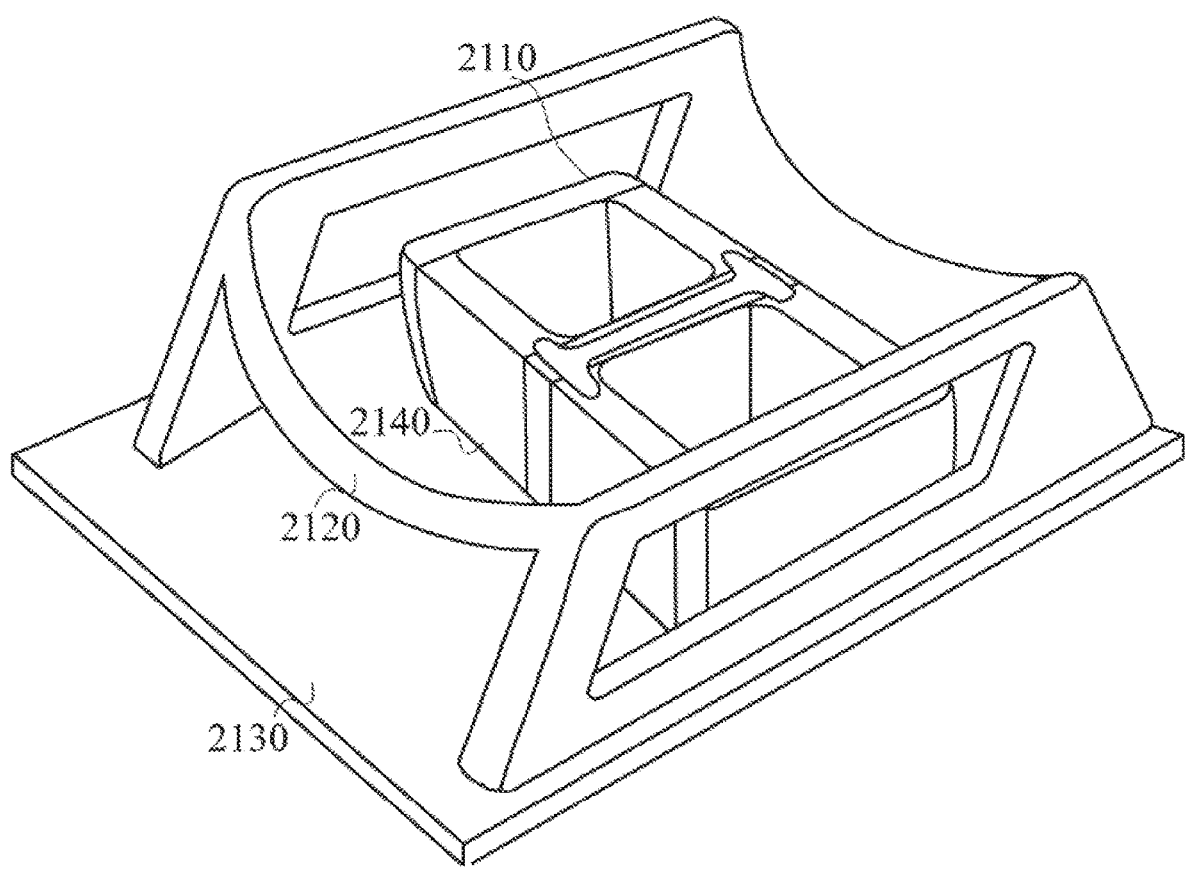
FIG. 21A is a schematic illustration of an exemplary embodiment of a pair of PET detectors according to one embodiment the present disclosure. Each PET detector contains 4 detection blocks and assumes the cubic column configuration.
Figure 21B:
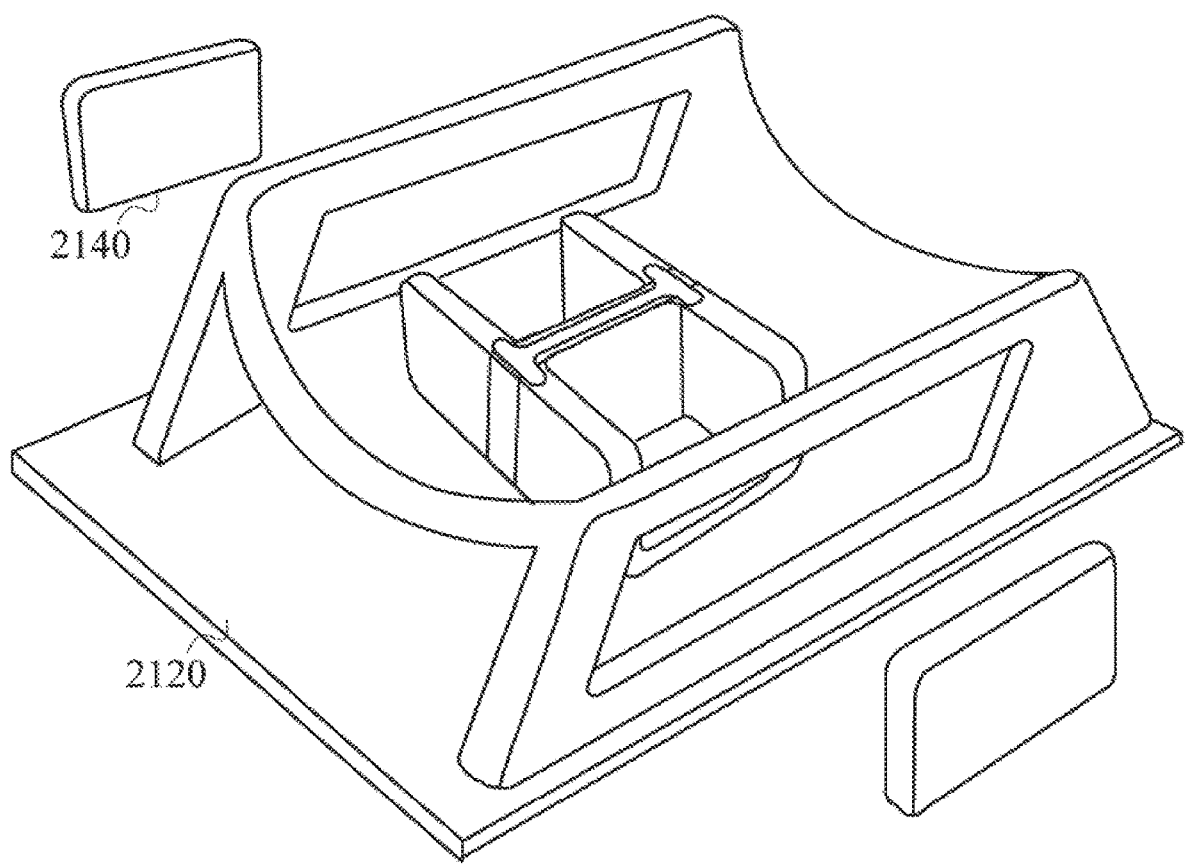
FIG. 21B is a schematic illustration of the situation where one detection block is removed from each PET detector of FIG. 17A, such that a sample area surrounded by the PET detector become accessible.
Figure 22:
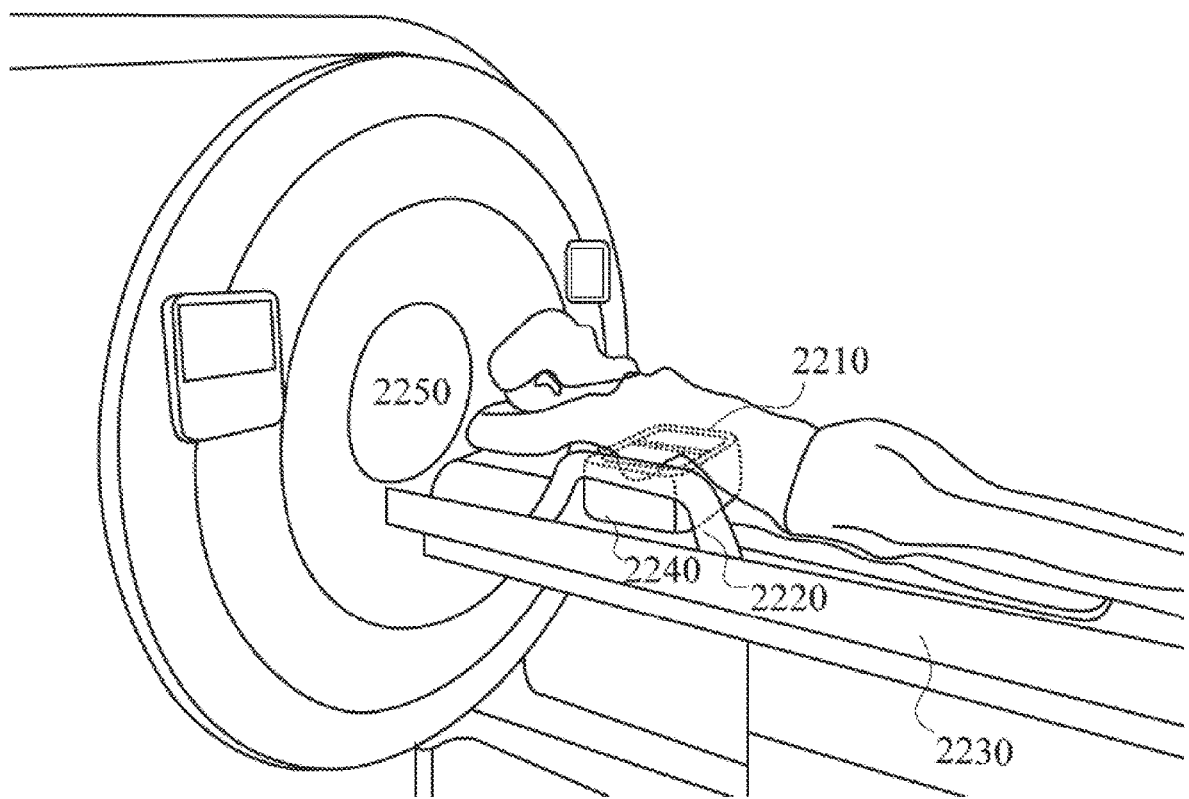
FIG. 22 illustrates a scenario where a human subject lies on a chest support with her breasts inserted into a sample area surrounded by PET detectors and MRI coil systems. In this exemplary embodiment, the chest support, the PET detectors and MRI coil systems are mounted on a patient bed, which can move the patient's body with respect to a MRI scanner.

Example 4.6—PET Detectors Integrated with Patient Support of Conventional MRI Scanner Particularly, FIG. 21 through FIG. 22 illustrates another specific embodiment of the PET/MRI insert integration. Particularly, FIG. 21A is a lateral view of the insert assembly. As shown in the figure, the insert assembly comprises a set of PET detectors (2110), a chest support (2120) and a patient support (2130). The set of PET detectors (2110) locates within the chest support (2120), and the assembly of the set of PET detectors (2110) and the chest support (2120) locate on the top of the patient support (2130) of the MR imaging modality.

As can be seen in the figure, the set of PET detectors (2110) comprises four separate PET detector blocks (2140); each of the PET detector block (2140) assumes a rectangular configuration. The four rectangular PET detector blocks (2140) forms a cube with a hollow space within the cube, and each of the PET detector forms a wall of said cube. In a particular embodiment, the PET detector block comprises an array of scintillators and an array of DSiPM photodetectors.

FIG. 21B is a lateral view of the insert assembly. Particularly, FIG. 21B illustrates two PET detector blocks removed from their original configuration. In a particular embodiment, one or more PET detector blocks are mounted removably onto the patient support (2130). More particularly, when a patient is examined using the PET/MRI multi-modality imaging system, the doctor could take advantage of the removable configuration of the PET detector blocks and perform imaging guided biopsy.

FIG. 22 illustrates a scenario where a female prepares to take a PET/MRI multi-modality scan. The female lies prone on the patient support (2230), with her chest supported by the chest support (2220). The target body, in this case each of the breasts of the female, is placed within the birdcage coil (2240) which is placed within the cube formed by four removably mounted PET detector blocks (2210). Once female is in the appropriate posture and her breasts are properly located in the birdcage coil (2240) and the PET detector assembly (2220), the patient support (2230) will carry the female into the MRI bore (2250) and the PET/MRI dual-modality scan begins.

Example 4.7—Integration of Control and Power System

Figure 23:
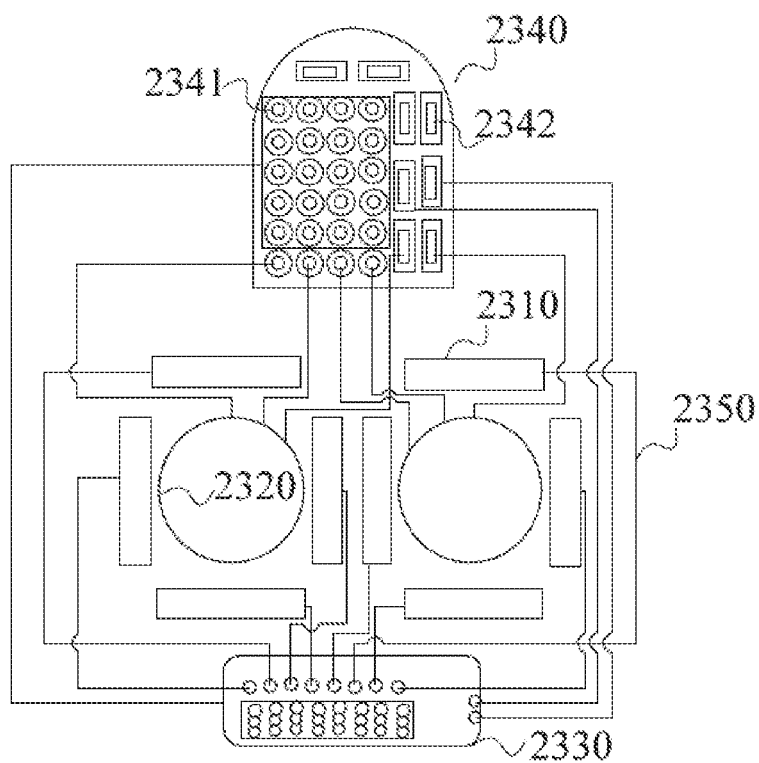
FIG. 23 is a schematic illustration of an exemplary embodiment of the control and power systems of a PET/MR hybrid system.

FIG. 23 is a schematic view of the cross-communication between the PET modality and MR modality in the PET/MR dual-modality imaging system. As shown in the figure, the PET detector assembly (2310) and breast coils (2320) are connected to PET control panel (2330) and MR control panel (2340) via wires (2350) respectively. Particularly, the PET detector assembly (2310) is connected to the PET control panel (2330) through input pins to transfer the detected signal to the PET control panel (2330). Meanwhile, the PET control panel (2330) provides power supply for the PET detector assembly (2310). Particularly, the breast coil (2320) is connected to MR control panel (2340) via signal interface (2341) to transfer the nuclear magnetic signals to the MR control panel (2330). And the MR control panel (2340) provides power supply for the breast coil (2320) via wires connected to its power interface (2342).

In some embodiments, the PET control panel (2330) and MR control panel (2340) may communicate directly. Particularly, the PET control panel (2330) is directly connected to the signal interface (2341) of the MR control panel (2340) to transfer the PET detection signals to the MR control panel (2340). Subsequently, the MR control panel transfers the signals of PET imaging and MR imaging to one or more processing units (not shown in the figure) to perform further data processing. Particularly, the MR control panel (2340) provides power supply for the PET control panel (2330) through the wires connected between the power interface (2342) of the MR control panel (2340) and the PET control panel.

In alternative embodiments, the MR control panel (2340) provides power supply for the PET control panel (2330) through wires connected in-between. The PET control panel may connect to one or more processing units (not shown in the figure) directly and transfer the imaging signals to the processing units for further data processing. And the MR control panel may connect to one or more processing units (not shown in the figure), either the same as the processing units to which the PET control panel connects or not, and transfer the imaging signals to the processing units for further data processing.

Example 5 PET Imaging Reconstruction Algorithms

In some embodiments, the ordered subsets expectation maximization (OSEM) algorithm is used for PET image reconstruction. The OSEM is an iterative method based on the theory that emission of annihilation is a Poisson process. The OSEM algorithm groups projection data into an ordered sequence of subsets (or blocks) and progressively processes every subset of the projections in each iteration process. Every subset updates the whole image intensity data and the image intensity data is updated k times when all the projecting data used (assume there are k subsets), and this is called a step. As such, the OSEM algorithm provides an order-of-magnitude acceleration of reconstructing image. An exemplary procedure for applying the OSEM algorithm is described in Hudson et al. *Accelerated image reconstruction using ordered subsets of projection data*. Medical Imaging, IEEE Transactions on, 1994, 13(4): 601-609, which document is incorporated herein by reference in its entirety.

Alternatively or additionally, in some embodiments, the filtered back projection (FBP) algorithm is applied to reconstruct PET images. Particularly, the FBP algorithm comprises backprojection procedures and filtering. More particularly, the FBP algorithm exploits a serious of projections of the target body that contains radioactive tracers in a specific distribution pattern. The projections of the distribution of the tracer molecules are taken by the PET detectors at different angles. The imaging processors run the projections back through the image to obtain a rough approximation of the original. The projections are superposed upon each other and interact constructively in regions that correspond to the distribution of the tracers in the original image. Optionally, a filter is used to eliminate potential blurring that occurs in other parts of the reconstructed image. In some embodiments, the filter is a ramp filter. An exemplary procedure for applying the FBP algorithm is described in Wang C X et al. *Performance evaluation of filtered backprojection reconstruction and iterative reconstruction methods for PET images*. Computers in biology and medicine, 1998, 28(1): 13-25, which document is incorporated herein by reference in its entirety.

Alternatively or additionally, in some embodiments, the maximum likelihood reconstruction of attenuation and activity (MLAA) algorithm is applied for image reconstruction. The MLAA algorithm estimates the activity and attenuation images from the emission data jointly. Particularly, MLAA incorporates a maximum-likelihood and maximum-a-posteriori reconstruction methodology. MLAA is based on the assumption that the tracer used herein has a uniform distribution throughout the target body and that emission of annihilation is a Poisson process. The MLAA algorithm uses an interleaved updating: in every iteration, first the activity is updated keeping the attenuation coefficients constant, and then vice versa. An exemplary procedure for applying the MLAA algorithm is described in Rezaei A, et al. *Simultaneous reconstruction of activity and attenuation in time-of-flight PET*. Medical Imaging, IEEE Transactions on, 2012, 31(12): 2224-2233, which document is incorporated herein by reference in its entirety.

Additionally or alternatively, in some embodiments, the Point Spread Function (PSF) algorithm is used for image reconstruction. The PSF algorithm is a kind of resolution modeling, which models the very phenomena that degrade resolution within the reconstruction algorithm. The PSF describes the response of an imaging system to a point source or point object. The PSF may be thought of as the extended blob in an image that represents an unresolved object. The degree of spreading (blurring) of the point object is a measure for the quality of an imaging system. In some embodiments, the image reconstruction is linear in power described by linear system theory. The point spread function may be independent of position in the object plane. Particularly, if there is no distortion, the image plane coordinates are linearly related to the object plane coordinates. An exemplary procedure for applying the PSF algorithm is described in Rahmim et al. *Resolution modeling in PET imaging: theory, practice, benefits, and pitfalls*. Medical physics, 2013, 40(6): 064301, which document is incorporated by reference herein.

The examples set forth above are provided to give those of ordinary skill in the art a complete disclosure and description of how to make and use the embodiments of the arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations that is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps. In particular, it will be understood that various modifications may be made without departing from the spirit and scope of the present disclosure. Accordingly, other embodiments are within the scope of the following claims.

What is claimed is:

1. A positron emission tomography (PET) detector comprising a plurality of detection blocks, each detection block having a scintillator face, wherein
    the scintillator face of each detection block opposes the scintillator face of at least one other detection block;
    the plurality of detection blocks flank a sample area for holding a target body; and
    each PET detector block comprises two scintillator crystal blocks, two angled light guides, a slotted light guide, and a photodetector.

2. The PET detector of claim 1, wherein the plurality of detection blocks form one or more opposing pairs of detection blocks.

3. The PET detector of claim 1, wherein the plurality of detection blocks comprises four detection blocks, and wherein the four detection blocks flank the sample area in a cubic column configuration with each detection block perpendicular to two other detection blocks.

4. The PET detector of claim 1, wherein the plurality of detection blocks comprises eight detection blocks, the eight detection blocks forming a first set of four detection blocks and a second set of four detection blocks, and wherein
    the sample area comprises a first sub-area and a second sub-area;
    the first set of four detection blocks flank the first sub-area in a cubic column configuration; and
    the second set of four detection blocks flank the second sub-area in a cubic column configuration.

5. The PET detector of claim 1, wherein the plurality of detection blocks comprises eight detection blocks, wherein the eight detection blocks flank the sample area in a barrel-shaped configuration with each detection block facing a separate octant of a 360 degree field.

6. The PET detector of claim 1, wherein at least one detection block is reversibly attached to the PET detector.

7. The PET detector of claim 1, wherein the two scintillator crystal blocks are axisymmetric about a middle line perpendicular to a horizontal surface of the photodetector block.

8. An insert system configured to reversibly attach to a main system having magnetic resonance imaging (MRI) function, the insert system comprising a positron emission tomography (PET) detector and a coil, wherein
    the PET detector comprises a plurality of detection blocks, each detection block having a scintillator face;
    the scintillator face of each detection block opposes the scintillator face of at least one other detection block;
    the coil surrounds a sample area for holding the target body;
    the plurality of detection blocks flank the coil; and
    each PET detector block comprises two scintillator crystal blocks, two angled light guides, a slotted light guide, and a photodetector.

9. The insert system of claim 8, wherein the coil comprising an RF transmitter and an RF receiver, the RF transmitter being adapted for delivering excitation electromagnetic radiation to the target body; the RF receiver being adapted for detecting nuclear magnetic resonance signal from the target body.

10. The insert system of claim 9, wherein the RF transmitter comprises a first coil system.

11. The insert system of claim 10, wherein the RF receiver comprises a second coil system.

12. The insert system of claim 11, wherein the first coil system and the second coil system are the same.

13. The insert system of claim 11, wherein one or both of the first coil system and the second coil system are multi-channel coils.

14. The insert system of claim 11, wherein one or both of the first coil system and the second coil system are phased-array coils.

15. The insert system of claim 8, further comprising a patient support, wherein the PET detector and the coil are mounted on the patient support.

16. The insert system of claim 15, wherein the patient support has a chest support having an approximate profile of a human patient's front chest with an opening for inserting the patient's breasts through.

17. The insert system of claim 8, wherein the coil includes an array coil system, and the coil is configured to transmit radiofrequency (RF) signal and receive magnetic resonance (MR) signal.

18. A multi-modality imaging system for analyzing a target body, the multi-modality imaging system comprising at least a PET imaging modality and an MR imaging modality, the PET imaging modality comprising an insert system comprising a PET detector and a coil, wherein
    the PET detector comprises a plurality of detection blocks, each detection block having a scintillator face;
    the scintillator face of each detection block opposes the scintillator face of at least one other detection block;
    the coil surrounds a sample area for holding the target body;

the plurality of detection blocks flank the coil; and each PET detector block comprises two scintillator crystal blocks, two angled light guides, a slotted light guide, and a photodetector.

19. The multi-modality imaging system of claim 18, wherein the MR imaging modality having a superconducting magnet and a body coil coaxially arranged and defining a bore for accommodating the target body, and the bore extending along a longitudinal direction;

the PET imaging modality insertable into the bore of the MR imaging modality, the sample area substantially extending along a vertical direction.

20. The multi-modality imaging system of claim 18, wherein the PET detector is configured to be reversibly attachable to a patient support of the multi-modality imaging system.

* * * * *